(12) United States Patent
Meserol et al.

(10) Patent No.: US 7,144,496 B2
(45) Date of Patent: Dec. 5, 2006

(54) BIOLOGICAL FLUID ANALYSIS DEVICE

(75) Inventors: Peter Meserol, deceased, late of Montville, NJ (US); by Shirley Meserol, legal representative, Montville, NJ (US); Andrey Ghindilis, Mukilteo, WA (US); Frank Pascale, Glen Cove, NY (US); Barry Wenz, Bedford, NY (US)

(73) Assignee: Pall Corporation, East Hills, NY (US)

( * ) Notice: Subject to any disclaimer, the term of this patent is extended or adjusted under 35 U.S.C. 154(b) by 537 days.

(21) Appl. No.: 10/415,035

(22) PCT Filed: Nov. 2, 2001

(86) PCT No.: PCT/US01/42903

§ 371 (c)(1),
(2), (4) Date: Apr. 23, 2003

(87) PCT Pub. No.: WO02/065087

PCT Pub. Date: Aug. 22, 2002

(65) Prior Publication Data

US 2004/0014023 A1   Jan. 22, 2004

Related U.S. Application Data

(63) Continuation-in-part of application No. 09/827,142, filed on Apr. 6, 2001, now abandoned.

(60) Provisional application No. 60/244,877, filed on Nov. 2, 2000.

(51) Int. Cl.
*G01N 27/327* (2006.01)

(52) U.S. Cl. ............... 205/792; 205/777.5; 204/403.01

(58) Field of Classification Search ........... 204/403.01, 204/403.15, 431; 205/792, 798.2, 798.5, 205/783
See application file for complete search history.

(56) References Cited

U.S. PATENT DOCUMENTS

| | | | |
|---|---|---|---|
| 3,837,745 A | 9/1974 | Acker et al. | |
| 3,837,746 A | 9/1974 | Acker et al. | |
| 3,868,223 A * | 2/1975 | Robock et al. | ............... 422/79 |
| 3,983,006 A | 9/1976 | Acker et al. | |
| 4,013,368 A | 3/1977 | Acker et al. | |
| 4,072,578 A | 2/1978 | Cady et al. | |
| 4,206,282 A * | 6/1980 | Hochstein | ................... 435/34 |
| 4,220,715 A | 9/1980 | Ahnell | |
| 4,317,879 A * | 3/1982 | Busby et al. | .......... 204/403.11 |
| 4,321,322 A | 3/1982 | Ahnell | |
| 4,507,119 A | 3/1985 | Spencer | |
| 4,666,853 A | 5/1987 | Meserol et al. | |
| 4,683,120 A | 7/1987 | Meserol et al. | |

(Continued)

FOREIGN PATENT DOCUMENTS

WO    WO 91/17809    11/1991

(Continued)

OTHER PUBLICATIONS

Derwent abstract of Bogdanovsk et al. (SU 877980 A) May 15, 1985.*

(Continued)

*Primary Examiner*—Alex Noguerola
(74) *Attorney, Agent, or Firm*—Leydig, Voit & Mayer, Ltd.

(57) ABSTRACT

A biological fluid analysis device (100) including a biosensor (50) comprising an electrochemical-enzymatic sensor including a working electrode (51) and a reference electrode (52), is disclosed.

26 Claims, 15 Drawing Sheets

U.S. PATENT DOCUMENTS

| | | | |
|---|---|---|---|
| 4,767,994 A | 8/1988 | Hopkins et al. | |
| 4,816,130 A | 3/1989 | Karakelle et al. | |
| 4,880,548 A | 11/1989 | Pall et al. | |
| 4,909,908 A | 3/1990 | Ross et al. | |
| 4,925,572 A | 5/1990 | Pall | |
| 4,947,339 A | 8/1990 | Czekajewski et al. | |
| 5,114,859 A * | 5/1992 | Kagenow | 436/50 |
| 5,126,054 A | 6/1992 | Matkovich | |
| 5,152,905 A | 10/1992 | Pall et al. | |
| 5,217,875 A | 6/1993 | Karpf et al. | |
| 5,328,823 A | 7/1994 | Spencer et al. | |
| 5,348,862 A | 9/1994 | Pasero et al. | |
| 5,443,743 A | 8/1995 | Gsell | |
| 5,451,321 A | 9/1995 | Matkovich | |
| 5,492,674 A | 2/1996 | Meserol | |
| 5,567,290 A | 10/1996 | Vadgama et al. | |
| 5,567,598 A | 10/1996 | Stitt et al. | |
| 5,573,649 A | 11/1996 | Sugama et al. | |
| 5,589,133 A | 12/1996 | Suzuki | |
| 5,670,060 A | 9/1997 | Matkovich et al. | |
| 5,672,484 A | 9/1997 | Eden et al. | |
| 5,746,898 A | 5/1998 | Preidel | |
| 5,804,401 A | 9/1998 | Gardiol et al. | |
| 5,922,616 A | 7/1999 | Dennison et al. | |
| 5,998,517 A | 12/1999 | Gentle, Jr. et al. | |
| 6,080,574 A | 6/2000 | Berndt | |
| 6,086,770 A | 7/2000 | Matkovich | |
| 6,103,033 A | 8/2000 | Say et al. | |
| 6,134,461 A | 10/2000 | Say et al. | |
| 6,344,333 B1 | 2/2002 | Gindilis | |
| 6,484,046 B1 | 11/2002 | Say et al. | |
| 6,555,333 B1 * | 4/2003 | Evalle | 435/34 |
| 6,607,501 B1 * | 8/2003 | Gorsuch | 604/5.01 |

FOREIGN PATENT DOCUMENTS

| | | |
|---|---|---|
| WO | WO 00/73778 | 12/2000 |
| WO | WO 00/73785 | 12/2000 |
| WO | WO 01/32828 A2 | 5/2001 |
| WO | WO 02/068580 A2 | 9/2002 |

OTHER PUBLICATIONS

CAPLUS abstract of v. Haebler et al. ("The action of sodium polyanethol sulfonate ("Liquoid") on blood cultures," Journal of Pathology and Bacteriology (1938), 46, 245-52).*

JPO abstract of Shibata et al. (JP 04346063 A) Dec. 1, 1992.*

"PTC" Thermistors for Self-Regulating Heaters, Advanced Thermal Products, Inc., Data Sheet P599 downloaded from www.atpsensur.com on May 18, 2001.

Ghindilis, et al. "Enzyme-Catalyzed Direct Electron Transfer: Fundamentals and Analytical Applications"; *Electroanalysis*, 1997, 9, No. 9, pp. 661-674.

* cited by examiner

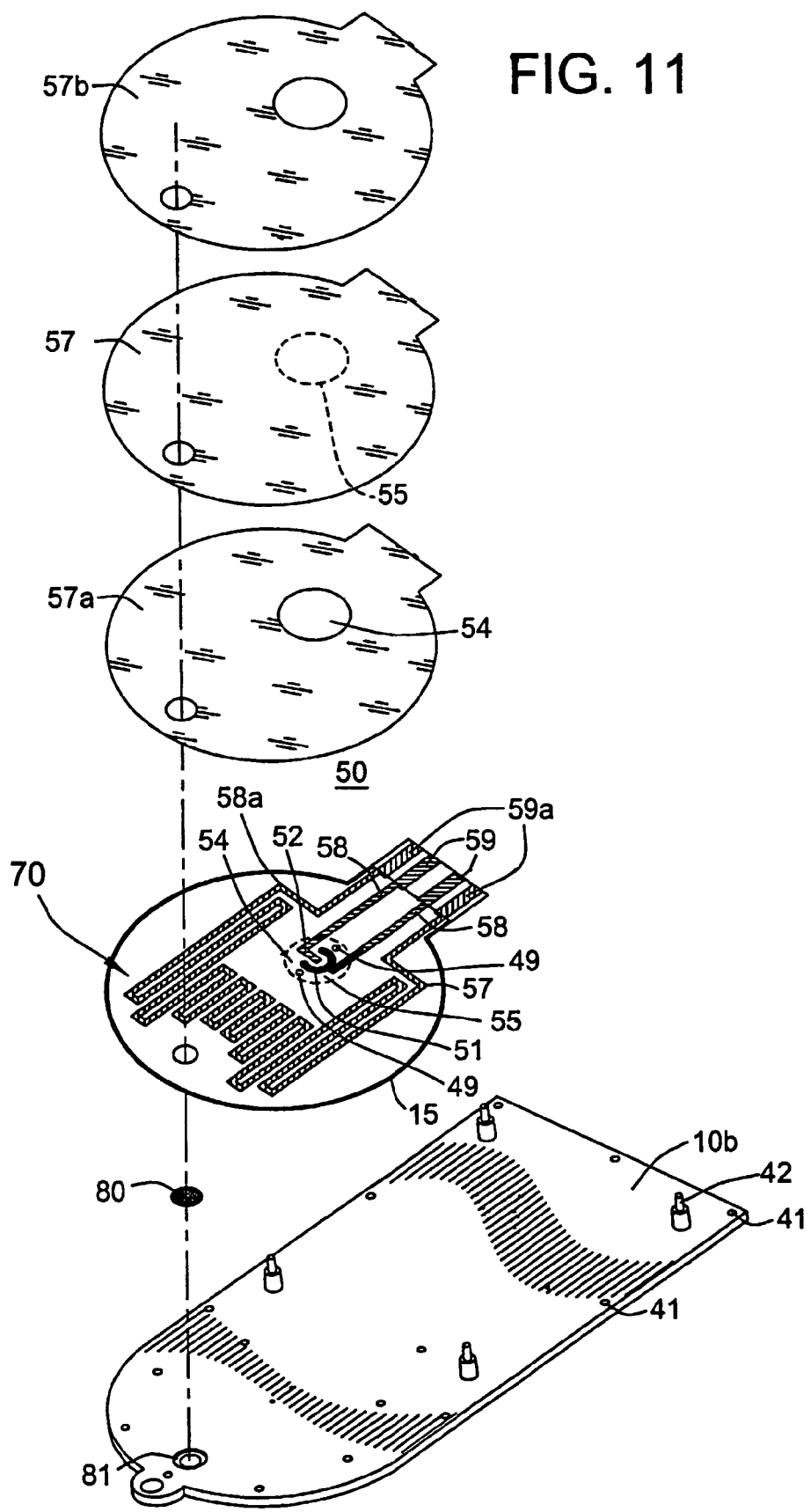

BIOLOGICAL FLUID ANALYSIS DEVICE

This application is a 371 of PCT/US01/142903, filed Nov. 02, 2001 and a continuation-in-part of U.S. application Ser. No. 09/827,142, abandoned, filed Apr. 06, 2001. It also claims priority from provisional application No. 60/244,877, filed Nov. 02, 2000.

TECHNICAL FIELD

This invention relates to a device for use with biological fluids such as blood and blood components that may be contaminated with microorganisms such as bacteria, wherein the device is arranged to detect oxygen consumption by the microorganisms.

BACKGROUND OF THE INVENTION

Blood is conventionally processed, e.g., separated into components, to provide a variety of valuable products such as transfusion products. Blood components or products such as buffy coat and platelets may be pooled during processing, e.g., 4–6 units of platelet concentrate can be pooled before administration as a transfusion product. Additionally, blood components processed in a closed system (e.g., without exposing the components to the outside environment) can be stored before administration. For example, red blood cells can be stored for several weeks, and platelets can be stored for several days (e.g., 5 days according to current U.S. practice).

Stored and/or non-stored components can include undesirable material such as bacteria. Bacteria can contaminate the blood or blood component during blood collection (including blood sampling) and/or storage. Other sources of contamination include the donor's blood, the environment (including the air, and the equipment in the environment), the donor's skin plug, and the phlebotomist.

Since some blood components (particularly platelets) are typically stored at ambient temperatures (e.g., about 22–26° C.), the problem of contamination may be magnified, as most bacteria reproduce more rapidly at ambient temperatures than at, for example, about 2–8° C.

Contaminated blood products, especially bacterially contaminated blood products, pose a potential health risk to those who come into contact with, or receive, these products. For example, the administration of transfusion products with bacterial contamination can have adverse affects on the recipient, and the administration of platelets with massive levels of bacterial contamination is implicated in about 150 cases of severe morbidity or death each year in the U.S.

Typical bacterial detection techniques include optical measures of turbidity or color changes correlated with growth of the bacteria. Bacterial detection techniques are generally labor- and time-intensive and may require expensive equipment. Some of the techniques may provide inaccurate results and/or may introduce contamination from the environment into the samples.

The present invention provides for ameliorating at least some of the disadvantages of the prior art. These and other advantages of the present invention will be apparent from the description as set forth below.

SUMMARY OF THE INVENTION

In accordance with an embodiment of the invention, a biological fluid analysis device is provided, the device comprising a housing including a biological fluid analysis chamber suitable for receiving a plasma-containing portion of biological fluid, the plasma-containing fluid possibly including microorganisms, and a biosensor communicating with the chamber, the biosensor comprising an electrochemical-enzymatic sensor for detecting (e.g., monitoring) oxygen consumption by the microorganisms. Preferably, the biological fluid analysis device further comprises a vent in communication with the analysis chamber.

In some embodiments, the biological fluid analysis device further comprises a heater suitable for raising the temperature of the plasma-containing fluid over the ambient temperature, preferably for a desired period of time to allow the microorganisms (if present) to reproduce more quickly. Illustratively, the heater can raise the temperature to about 35° C. for at least about 4 hours, or maintain the temperature in the range of from about 30° C. to about 37° C., more preferably in the range from 32° C. to 35° C., for at least about 4 hours.

Additionally, a biological fluid processing system is provided according to an embodiment of the invention, the system comprising a biological fluid analysis device, preferably including a heater, and at least one container such as a flexible blood bag in fluid communication with the device. In a more preferred embodiment, the system includes, interposed between the container and the analysis device, a filter that allows a microorganism- and plasma-containing portion of biological fluid to pass from the blood bag into the analysis chamber of the analysis device, while reducing the passage of at least one of platelets, red blood cells and white blood cells therethrough.

In accordance with another embodiment of the invention, a biological fluid processing arrangement is provided, comprising a biological fluid analysis device comprising a housing including a biological fluid analysis chamber suitable for receiving a plasma-containing portion of biological fluid, a vent communicating with the analysis chamber, and a biosensor comprising an electrochemical-enzymatic sensor for detecting the oxygen concentration in the analysis chamber, wherein the biosensor communicates with the analysis chamber; and, in fluid communication with the device, a filter, the filter allowing a microorganism- and plasma-containing portion of biological fluid to pass (e.g., from a source and/or storage container such as a blood bag) into the analysis chamber, while reducing the passage of at least one of platelets, red blood cells and white blood cells therethrough. In one preferred embodiment, the arrangement further comprises a heater suitable for raising the temperature of the plasma-containing fluid, as described above.

Typically, the biological fluid processing system, more preferably, the biological fluid analysis device itself, includes one or more signal generators such as visible markers (e.g., indicator lamps), wherein the one or more signal generators generate signals indicating, for example, the concentration or change in concentration of oxygen and/or indicating the oxygen concentration is being monitored. Even more preferably, the device includes a self-contained power source such as at least one battery, and the device is arranged to allow the oxygen concentration and/or the change in oxygen concentration to be detected for a desired period of time. For example, in some embodiments wherein the biological fluid in the source and/or storage container comprises platelets (e.g., platelet concentrate or pooled platelets), the device allows the oxygen concentration to be detected for up to about 8 days, or more.

A method according to an embodiment of the instant invention includes providing a plasma-containing portion of biological fluid, the plasma-containing fluid possibly including microorganisms, and detecting the oxygen consumption by the microorganisms using a biosensor comprising an electrochemical-enzymatic sensor arranged to detect the oxygen concentration. Typically, the oxygen concentration is monitored over a period of time, e.g., at least about a 4 hour period of time, more typically, at least about a 6 hour period of time. Preferably, if the oxygen concentration decreases over a period of time, a signal is generated when the decrease in the oxygen concentration reaches a preset reference value, a threshold value, or an algorithm calculation.

In a preferred embodiment, the method includes providing a filtered plasma-containing sample of biological fluid in a biological fluid analysis chamber, wherein microorganisms in the filtered sample, if present, consume oxygen, and the oxygen consumption is subsequently detected using the biosensor. In a more preferred embodiment, the filtered, possibly microorganism-containing sample comprises a plasma-rich, possibly bacteria-containing, platelet-reduced fluid, and the change in the oxygen concentration in the chamber (e.g., the oxygen consumption by the bacteria) is monitored over a desired period of time.

In some embodiments, the method also comprises raising the temperature of the plasma-containing sample of biological fluid to a temperature at which the microorganisms reproduce more rapidly, and detecting the oxygen consumption by the microorganisms in the plasma-containing sample.

Devices, systems and methods according to the present invention are especially suitable for use by transfusion services, blood centers and/or blood bank personnel.

The present invention is particularly advantageous in providing early detection of clinically significant levels of bacteria in platelet-containing biological fluid.

BRIEF DESCRIPTION OF THE DRAWINGS

FIG. 4 shows various cross-sectional views of an embodiment of the assembled device shown in FIG. 3, wherein the portions of the housing have been assembled.

FIG. 6 shows various views of another embodiment of the analysis device (wherein the device includes a heater), as well as showing various views of the analysis device housing.

FIG. 8 shows various views of another embodiment of an assembled device.

FIG. 11 shows the embodiment of the biosensor and heater as illustrated in FIG. 10, disposed on the bottom section of the housing.

SPECIFIC DESCRIPTION OF THE INVENTION

Figure 1:
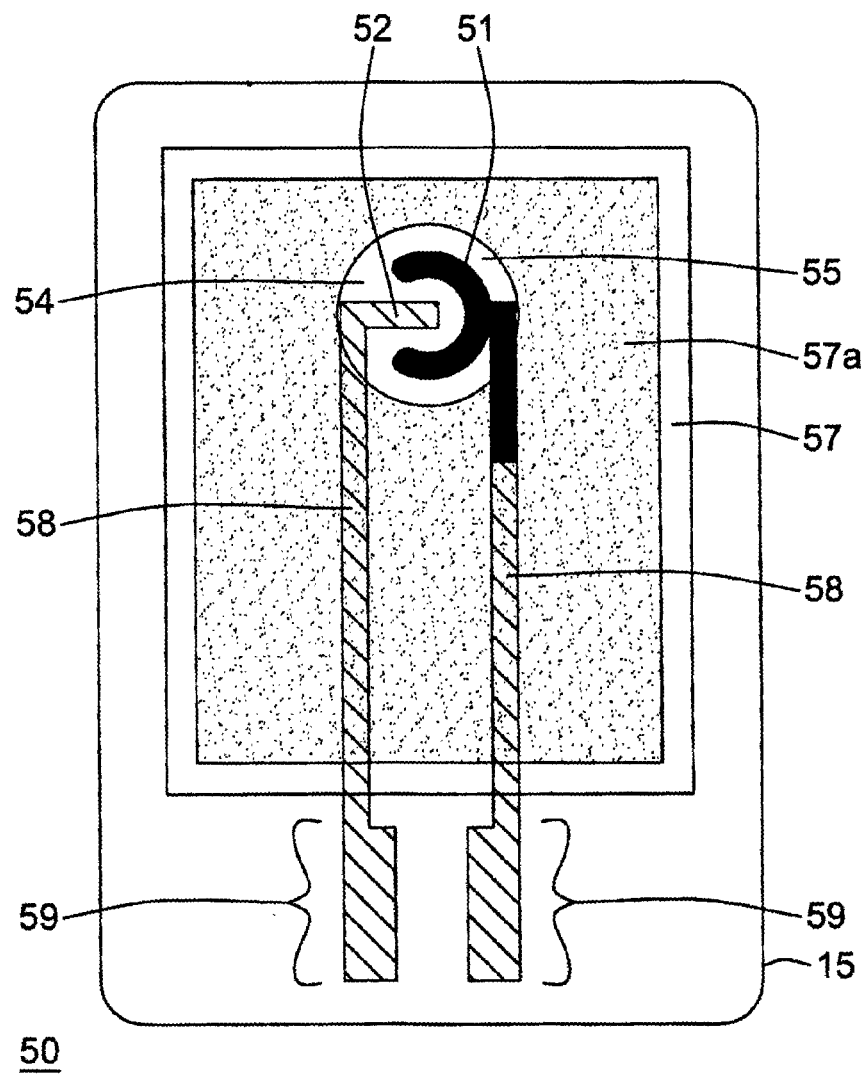
FIG. 1 shows an embodiment of a biosensor according to the invention, including a working electrode, a reference electrode, an electrode chamber, an electrode cover, and an insulator element, wherein the biosensor is disposed on a support member.

In accordance with an embodiment of the invention, a biological fluid analysis device is provided comprising a housing including a biological fluid analysis chamber suitable for receiving a plasma-containing portion of biological fluid, the plasma-containing fluid possibly including microorganisms; a vent communicating with the analysis chamber, the vent comprising a porous medium having a bacterial blocking pore rating; and a biosensor communicating with the analysis chamber, the biosensor comprising an electrochemical-enzymatic sensor including a working electrode and a reference electrode, wherein the biosensor is arranged to detect the oxygen concentration in the analysis chamber. In a more preferred embodiment, a biological fluid processing system comprises the biological fluid analysis device in fluid communication with a container suitable for holding a biological fluid, and in an even more preferred embodiment, the biological fluid processing system further comprises a filter (e.g., in a housing to provide a filter assembly) allowing a microorganism- and plasma-containing portion of biological fluid to pass into the analysis chamber, while reducing the passage of at least one of platelets, red blood cells and white blood cells therethrough, interposed between the container and the biological fluid analysis device.

In another embodiment, a biological fluid processing arrangement comprises a biological fluid analysis device comprising a housing comprising a biological fluid analysis chamber suitable for receiving a plasma-containing portion of biological fluid, the plasma-containing fluid possibly including microorganisms, and a biosensor communicating with the chamber, the biosensor comprising an electrochemical-enzymatic sensor including a working electrode and a reference electrode, wherein the biosensor is arranged to detect the oxygen concentration in the analysis chamber; and, in fluid communication with the analysis device, a filter, the filter allowing a microorganism- and plasma-containing portion of biological fluid to pass (e.g., from a blood bag) into the analysis chamber, while reducing the passage of at least one of platelets, red blood cells and white blood cells therethrough.

Typically, the oxygen concentration and/or the change in the oxygen concentration in the analysis chamber is monitored over a predetermined period of time, e.g., at least about a 4 hour period of time, more typically, at least about a 6 hour period of time, and in some embodiments, at least about a 12 hour period of time. Embodiments of the invention include monitoring the oxygen concentration and/or the change in the oxygen concentration in the analysis chamber for at least about a 24 hour period of time, or for at least about a 48 hour period of time, or more.

In some embodiments, a signal is generated to indicate the oxygen concentration is being monitored. In a preferred embodiment, if the oxygen concentration decreases over a period of time, a signal is generated when the decrease in the oxygen concentration reaches a preset reference value, a threshold value, or an algorithm calculation. In one embodiment, at least two signals are generated, one signal indicating the oxygen concentration is being monitored, and at least another signal indicating either the oxygen concentration has decreased to a preset reference value, a threshold value, or an algorithm calculation (and thus, a clinically significant level of microorganisms is present), or the oxygen concentration has not decreased to a preset reference value, a threshold value, or an algorithm calculation (and thus, a clinically significant level of microorganisms is not present).

Preferably, embodiments of the invention include a heater arranged to raise the temperature of the plasma-containing fluid in the chamber to at least about 30° C. or more for any desired period of time, e.g., for at least about 2 hours, or, for example, for at least the period of time for monitoring the oxygen concentration and/or the change in the oxygen concentration as described above, e.g., for at least about 4 hours, at least about 6 hours, at least about 12 hours, and in some embodiments, at least about 24 hours, or at least about 48 hours, or more. Since some microorganisms, especially some bacteria, reproduce more rapidly at a temperature of about 30° C. or more (e.g., a temperature in the range of 32° C. to 35° C.), these embodiments can allow the microorganisms to grow to a detectable level more quickly.

Methods for using embodiments of the biological fluid analysis device, the biological fluid processing arrangement, and the biological fluid processing system are also provided by the present invention.

A method according to an embodiment of the instant invention includes providing a plasma-containing portion of biological fluid, the plasma-containing fluid possibly including microorganisms, and detecting the oxygen consumption by the microorganisms using a biosensor comprising an electrochemical-enzymatic sensor arranged to detect the oxygen concentration. The oxygen concentration and/or change in concentration (e.g., a decrease in the concentration due to consumption by the microorganisms) can be monitored over any desired period of time. Preferably, the method includes generating at least two signals, one signal indicating the oxygen concentration is being monitored, and at least another signal indicating either the oxygen concentration has decreased to a preset reference value, a threshold value, or an algorithm calculation (and thus, a clinically significant level of microorganisms is present), or that the oxygen concentration has not decreased to a preset reference value, a threshold value, or an algorithm calculation (and thus, a clinically significant level of microorganisms is not present).

In accordance with a preferred embodiment of the invention, the biological fluid analysis device including the biosensor is utilized with a filtered biological fluid, wherein the filtered biological fluid possibly contains microorganisms and has been depleted of a level of at least one of platelets, white blood cells and red blood cells, and the filtered fluid is to be analyzed for the presence of microorganisms by detecting the decrease in oxygen concentration due to oxygen consumption by the microorganisms.

For example, the analysis device including the biosensor according to the present invention is particularly suitable for use in detecting the level or concentration of oxygen consumed by bacteria, since components of the biological fluid (particularly platelets) consume oxygen, and thus the reduction or elimination of other components of the biological fluid as the fluid passes through the filter reduces the potential for "noise" (particularly background noise) in the analysis chamber. Since the background noise (e.g., oxygen consumption that could be attributed to the metabolism of the platelets) is reduced, "bacteria consumed oxygen" can be more accurately monitored in the analysis chamber.

Moreover, the biosensor according to the invention is especially advantageous and sensitive for this application, since it detects the oxygen concentration initially, and allows the decreasing level to be monitored. In contrast, some detection systems, e.g., measuring increases in turbidity, require the substance being measured to reach a threshold level before it can be detected.

As microorganisms (especially bacteria) can be detected in accordance with the invention, embodiments of the present invention can be suitable for providing blood components that can be stored for longer periods than are currently allowed by the regulations in various countries. For example, due, at least in part, to fears that platelet concentrate (PC) can be contaminated with bacteria, current U.S. practice requires that individual units of PC be utilized within 5 days, and pooled PC be utilized within 8 hours of pooling. However, since embodiments of the invention allow the detection of contaminated PC, pooled and unpooled PC can be monitored, and if determined to be uncontaminated, can be used after the 5 day/8 hour limits that are currently required. Illustratively, individual units of PC or pooled PC can be transfused after, for example, 7 days of storage.

The following definitions are used in accordance with the invention.

Biosensor. A biosensor refers to an electrochemical-enzymatic sensor, preferably a two electrode electrochemical-enzymatic sensor, utilizing at least one enzyme to catalyze the electroreduction of oxygen. In a preferred embodiment, the enzyme catalyzes the reaction directly, i.e., without a mediator. Laccase is the preferred electrocatalytically active enzyme for carrying out the invention. Other suitable electrocatalytically active oxidoreductases include bilirubin oxidase and ascorbate oxidase. Suitable enzymes are commercially available, e.g., from Sigma Chemical Co. (St. Louis, Mo.).

The biosensor includes a working electrode (sometimes referred to as an actual measuring electrode) and a reference electrode, allowing potentiometric measurement. In less preferred embodiments, the biosensor includes a counter electrode.

A biosensor that detects oxygen utilizes electrons that are transferred, preferably directly, from the working or actual electrode to the oxygen molecule via the active site of the enzyme.

The enzyme laccase catalyzes electroreduction of oxygen directly due to a catalytic reduction of over voltage, as represented by the following reaction:

$$O_2 + 4H^+ + 4e^- \rightarrow 2H_2O.$$

Illustratively, a biosensor including laccase, when exposed to an increased concentration of atmospheric oxygen, exhibits an observable increase in electrode potential, e.g., an increase ≧300 mV above the level of the reference electrode, due to the transfer of electrons directly from the working electrode to atmospheric oxygen via the laccase active site.

A biosensor including laccase, when exposed to a decreased concentration of oxygen, exhibits an observable decrease in electrode potential, i.e., the potential decreases from a typical initial value of about 300 mV or more (more typically, an initial value in the range of from about 350 mV to about 500 mV) toward the level of the reference electrode (a laccase-free electrode). The voltage drop is approximately proportional to the decrease in oxygen concentration.

Working Electrode. A working electrode is an electrode at which the substance of interest is electroreduced, preferably without an electron transfer agent (e.g., a redox mediator).

Reference Electrode. A reference electrode is an electrode used as a standard relative to which a varying potential can be measured.

Counter Electrode. A counter electrode is an electrode paired with the working electrode, through which passes a current equal in magnitude and opposite in sign to the current passing through the working electrode.

Biological Fluid. A biological fluid includes any treated or untreated fluid associated with living organisms, including, but not limited to, blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), platelet-rich plasma (PRP), platelet-poor plasma (PPP), platelet-free plasma, plasma, fresh frozen plasma (FFP), components obtained from plasma, packed red cells (PRC), transition zone material or buffy coat (BC); analogous blood products derived from blood or a blood component or derived from bone marrow; red cells separated from plasma and resuspended in physiological fluid or a cryoprotective fluid; and platelets separated from plasma and resuspended in physiological fluid or a cryoprotective fluid. The biological fluid may have been treated to remove some of the leukocytes before being processed according to the invention. As used herein, blood product or biological fluid refers to the components described above, and to similar blood products or biological fluids obtained by other means and with similar properties.

A "unit" is the quantity of biological fluid from a donor or derived from one unit of whole blood. It may also refer to the quantity drawn during a single donation. Typically, the volume of a unit varies, the amount differing from patient to patient and from donation to donation. Multiple units of some blood components, particularly platelets and buffy coat, may be pooled or combined, typically by combining four or more units.

As used herein, the term "closed" refers to a system that allows the collection and processing (and, if desired, the manipulation, e.g., separation of portions, separation into components, filtration, storage, and preservation) of biological fluid, e.g., donor blood, blood samples, and/or blood components, without the need to compromise the sterile integrity of the system. A closed system can be as originally made, or result from the connection of system components using what are known as "sterile docking" devices. Illustrative sterile docking devices are disclosed in U.S. Pat. Nos. 4,507,119, 4,737,214, and 4,913,756.

Microorganisms. Microorganisms comprise protozoa and/or bacteria, including gram-positive and gram-negative bacteria. Illustrative bacteria include, but are not limited to *Staphylococcus epidermidis, Staphylococcus aureus, Serratia marcescens, Serratia liquefaciens, Yersinia enterocolitica, Klebsiella pneumoniae, Klebsiella oxytoca, Escherichia coli, Enterobacter cloacae, Enterobacter aerogenes, Pseudomonass aeruginoisa, Salmonella* spp., *Bacillus* spp., such as *Bacillus cereus,* Group B streptococcus, and *coagulase negative staphylococci.*

Each of the components of the invention will now be described in more detail below, wherein like components have like reference numbers.

FIG. 1 shows an embodiment of a biosensor 50 comprising a working electrode 51, and a reference electrode 52 (each electrode further comprising a conductive trace 58) disposed in an electrode chamber 54, the biosensor also comprising an electrode cover 57 comprising a gas permeable element 55 covering the electrode chamber 54, and an insulator element 57a interposed between the electrode cover 57 and the upper surfaces of the conductive traces 58 of the electrodes 51 and 52, wherein the biosensor is disposed on a support member 15. The insulator element 57a is arranged so that a portion of the electrode cover 57 is not blocked or covered by the insulator element 57a, and this unblocked or uncovered portion of the electrode cover 57 forms the gas permeable element 55.

Figure 2:
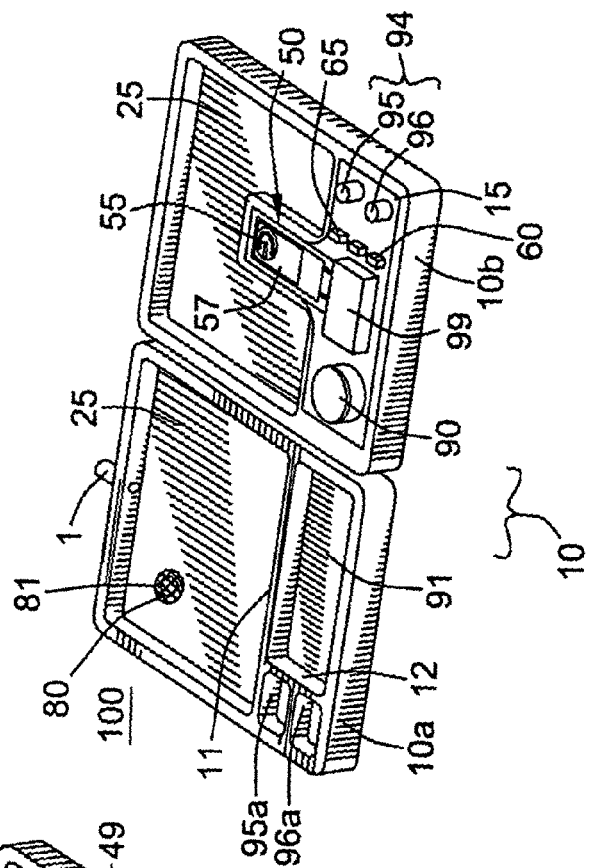
FIG. 2 is an exploded view of an embodiment of the biological fluid analysis device according to the present invention, comprising a housing having a first housing portion and a second housing portion, the housing including an analysis chamber and an inlet port; a biosensor as illustrated in FIG. 1; a power source, a processing unit, and two indicator lamps.

The embodiment illustrated in FIG. 2 shows an exploded internal view of a biological fluid analysis device 100, the device comprising a housing 10 having a first section 10a and a second section 10b, the housing including a biological fluid analysis chamber 25 having an internal volume suitable for receiving a plasma-containing portion of biological fluid, an inlet port 1, a vent 80 and a vent port 81, in fluid communication with the analysis chamber 25; a biosensor 50 comprising a working electrode 51 and a reference electrode 52 disposed in an electrode chamber 54, an insulator element 57a disposed on an electrode cover 57 comprising a gas permeable element 55 covering the electrode chamber 54, a power source 90, a processing unit 99, and a visible marker 94 comprising two indicator lamps 95 and 96, disposed on a support member 15.

Figure 3:
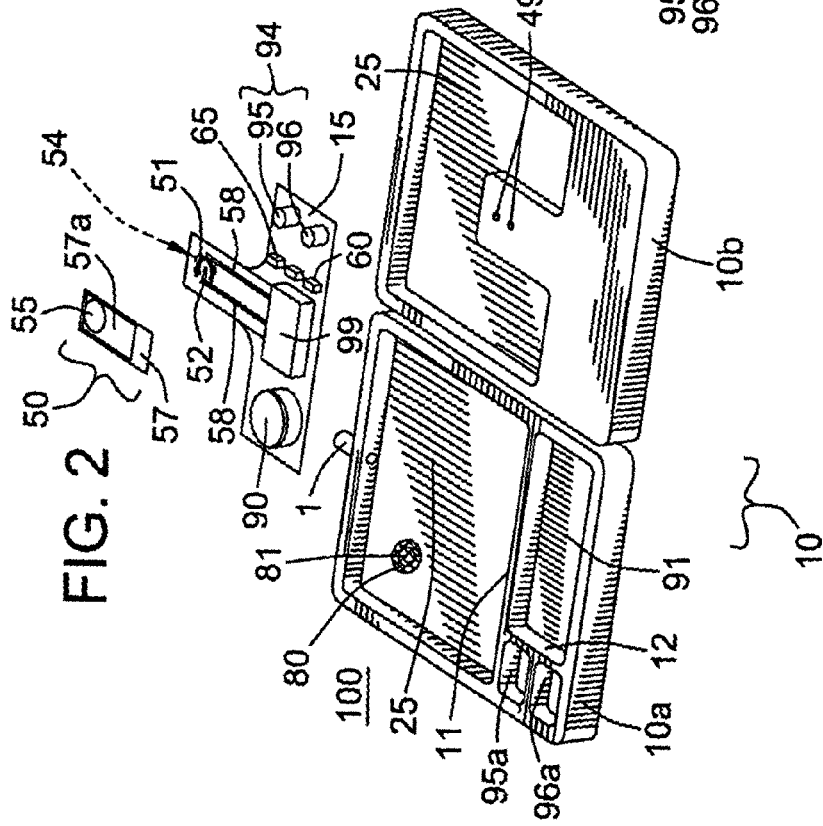
FIG. 3 illustrates an internal view of the analysis device shown in FIG. 2, wherein the biosensor, power source, processing unit, and indicator lamps have been assembled in the housing.

FIG. 3 shows another exploded internal view of the analysis device 100 as described in FIG. 2 wherein the biosensor 50 has been assembled in the housing 10.

Figure 4A:
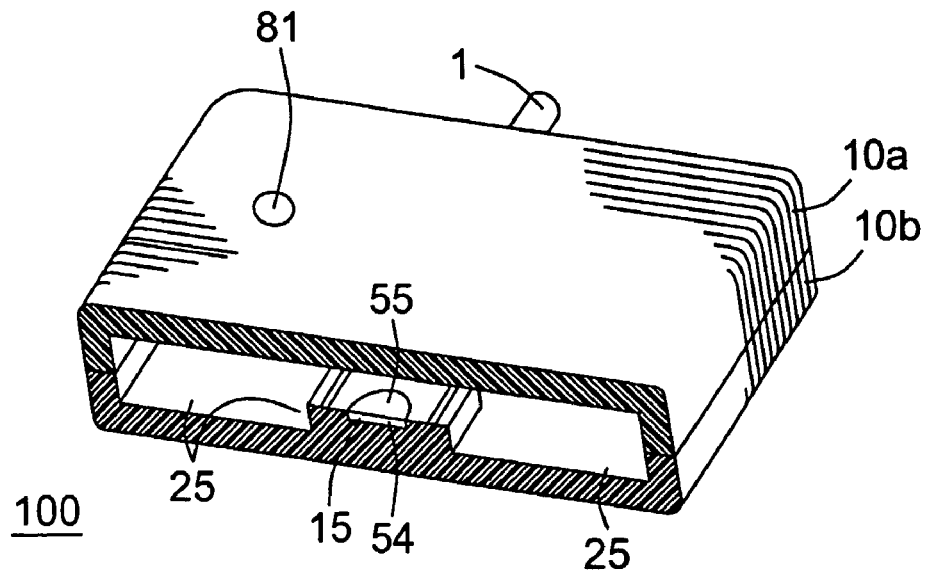
FIG. 4a shows a cross-sectional sidewise view.
Figure 4B:
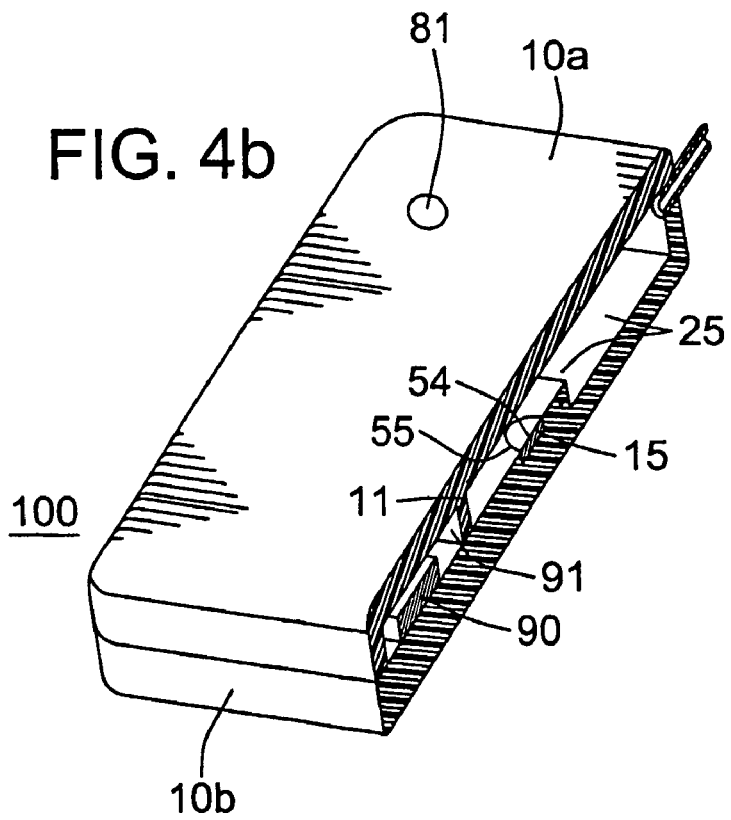
FIG. 4b shows a cross-sectional lengthwise view.

FIGS. 4a and 4b show cross-sectional views of an embodiment of the analysis device shown in FIG. 3, wherein the housing 10 has been assembled and biosensor 50 communicates with the interior volume of analysis chamber 25.

Figure 5:
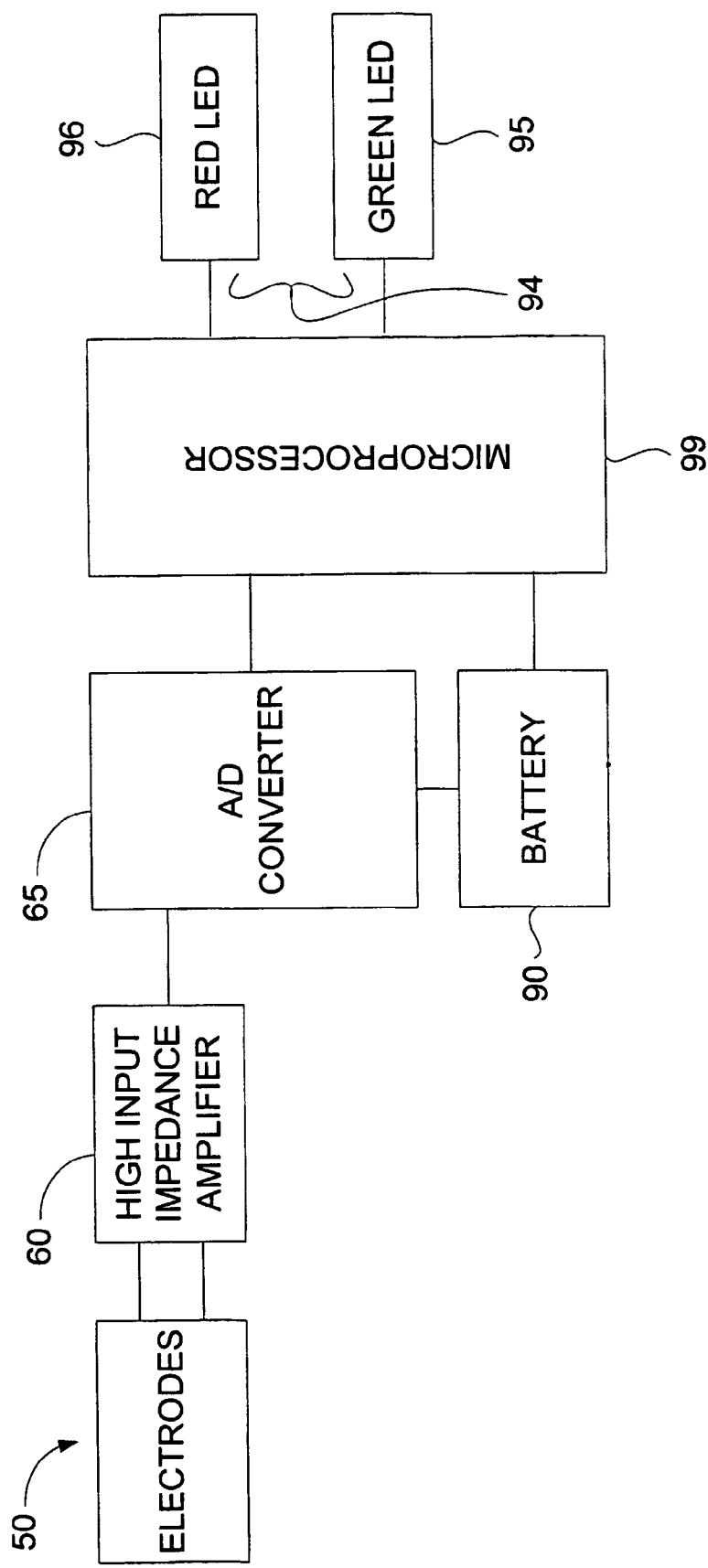
FIG. 5 is a block diagram in accordance with one embodiment of a biological fluid analysis device according to the invention.

FIG. 5 is a block diagram in accordance with one embodiment of a biological fluid analysis device according to the invention, showing the relationship between the electrodes of the biosensor 50, a high impedance amplifier 60, an analog-to-digital converter 65, the processing unit 99 (comprising a microprocessor), and a signal generator such as a visible marker 94 including multiple elements (comprising indicator lamps 95 and 96 such as light emitting diodes (LEDs)). The power source 90 provides the power to operate the high impedance amplifier 60, the analog-to-digital converter 65, the processing unit 99 and the indicator lamps 95 and 96.

FIG. 6 shows various views of another embodiment of the biological fluid analysis device 100 and the device housing 10, wherein the housing includes housing sections 10a, 10b, 10c, and 10d. FIG. 6a shows an oblique view of the device 100 (with the battery cover 10c inserted); FIG. 6b shows an exploded view of the device 100 comprising housing sections 10a, 10b, 10c, and 10d; biosensor 50, analysis chamber seal 25a, power source 90, processing unit 99 comprising a microprocessor, and a visible marker 94 including indicator lamps 95 and 96. FIG. 6c shows an exploded view of the analysis device housing 10 comprising housing sections 10a, 10b, 10c, and 10d; FIG. 6d shows a cross-sectional side view of the housing 10 with the battery cover opened, wherein an analysis chamber seal 25a is interposed between the analysis chamber 25 (part of housing section 10a) and housing section 10b, and a heater 70 is associated with housing section 10b. FIG. 6e shows a bottom view of the bottom section of the housing 10b for receiving a heater 70, FIG. 6f shows a top view of the bottom section of the housing 10b for receiving the biosensor, wherein the biosensor would be disposed at region 48 (biosensor not shown), and FIG. 6g shows a bottom view of the top section of the housing, including the analysis chamber 25 wherein analysis chamber seal 25a is also shown.

Figure 7:
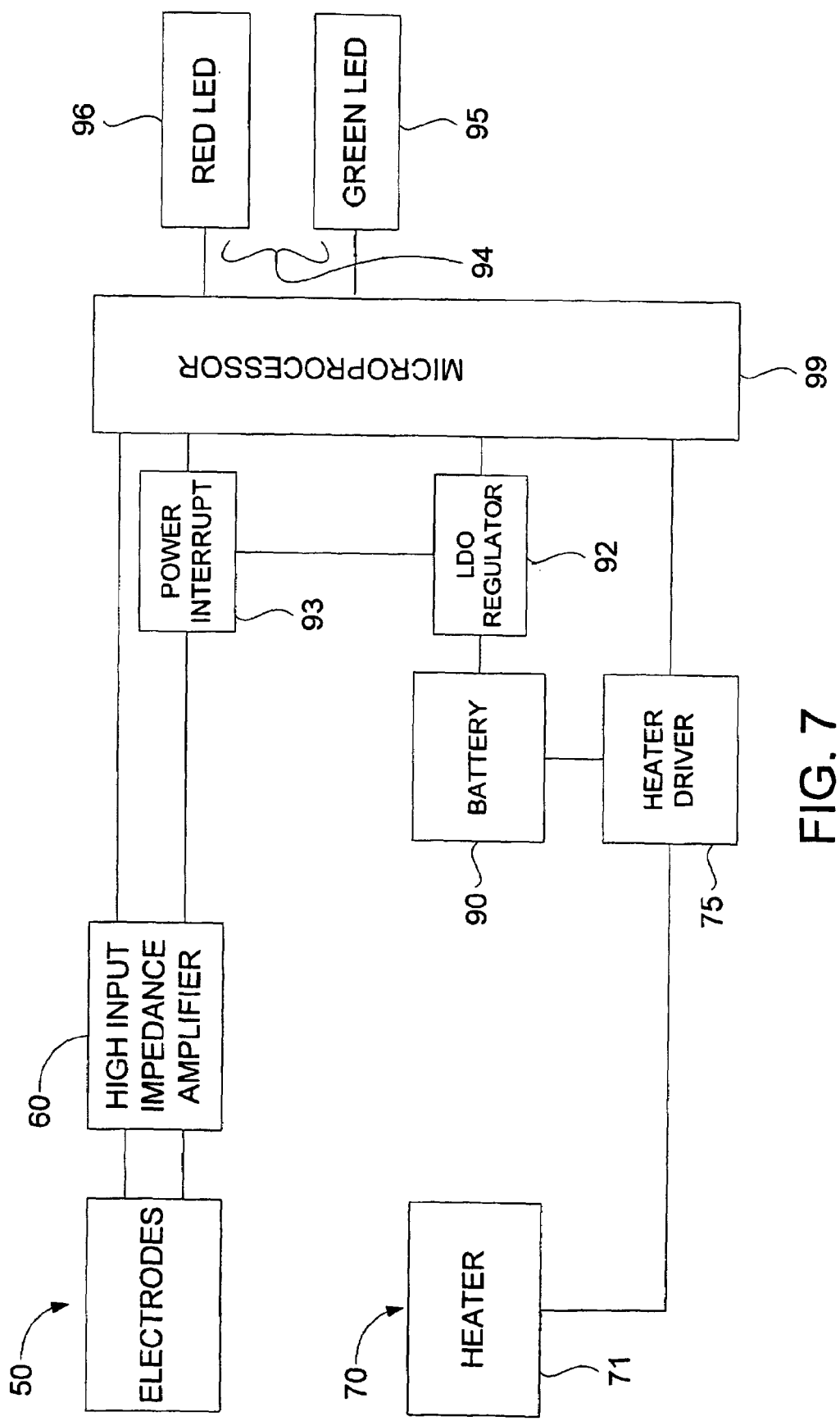
FIG. 7 is a block diagram in accordance with an embodiment of a biological fluid analysis device according to the invention, wherein the device includes a heater.

FIG. 7 is a block diagram in accordance with one embodiment of a biological fluid analysis device according to the invention, wherein the device includes a heater, showing the relationship between the electrodes of the biosensor 50, the high impedance amplifier 60, the processing unit 99 (comprising a microprocessor), and a signal generator such as the visible marker 94 including multiple elements (comprising indicator lamps 95 and 96, illustrated as LEDs). In this embodiment, the analog-to-digital conversion is executed by software in processing unit 99. The heater 70 (comprising a thermistor 71) is turned on and off by a heater driver 75, that is in turn, controlled by the software in the processing unit 99. The power source 90 provides the power to operate the high impedance amplifier 60, the processing unit 99, the indicator lamps 95 and 96, and the heater 70. In this diagram, a low-drop out voltage regulator 92 interposed between the power source and the microprocessor insures the processing unit 99 always has stable voltage to operate even with a weak battery, and a power interrupt 93 between the high impedance amplifier 60 and the processing unit 99 provides additional control of power consumption by turning off the high impedance amplifier between readings.

Figure 8A:
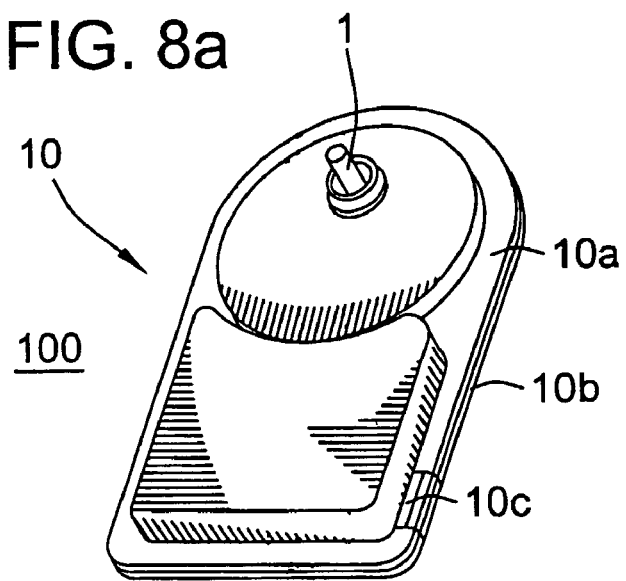
FIG. 8a shows an oblique view.
Figure 8B:
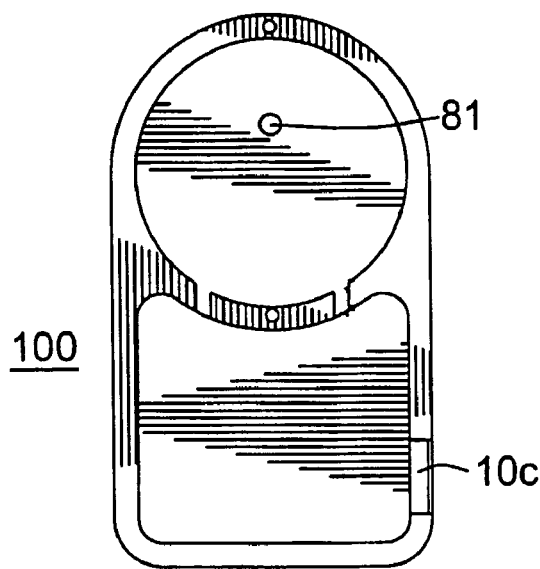
FIG. 8b shows a rear view.
Figure 8C:
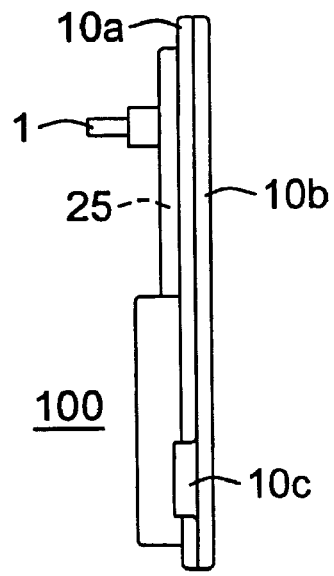
FIG. 8c shows a side view.

FIGS. 8a–8c show embodiments of an assembled device 100 wherein the first and second sections 10a, 10b of the housing 10 have been sealed together to provide a liquid tight seal, and the device includes a battery cover 10c.

Figure 9:
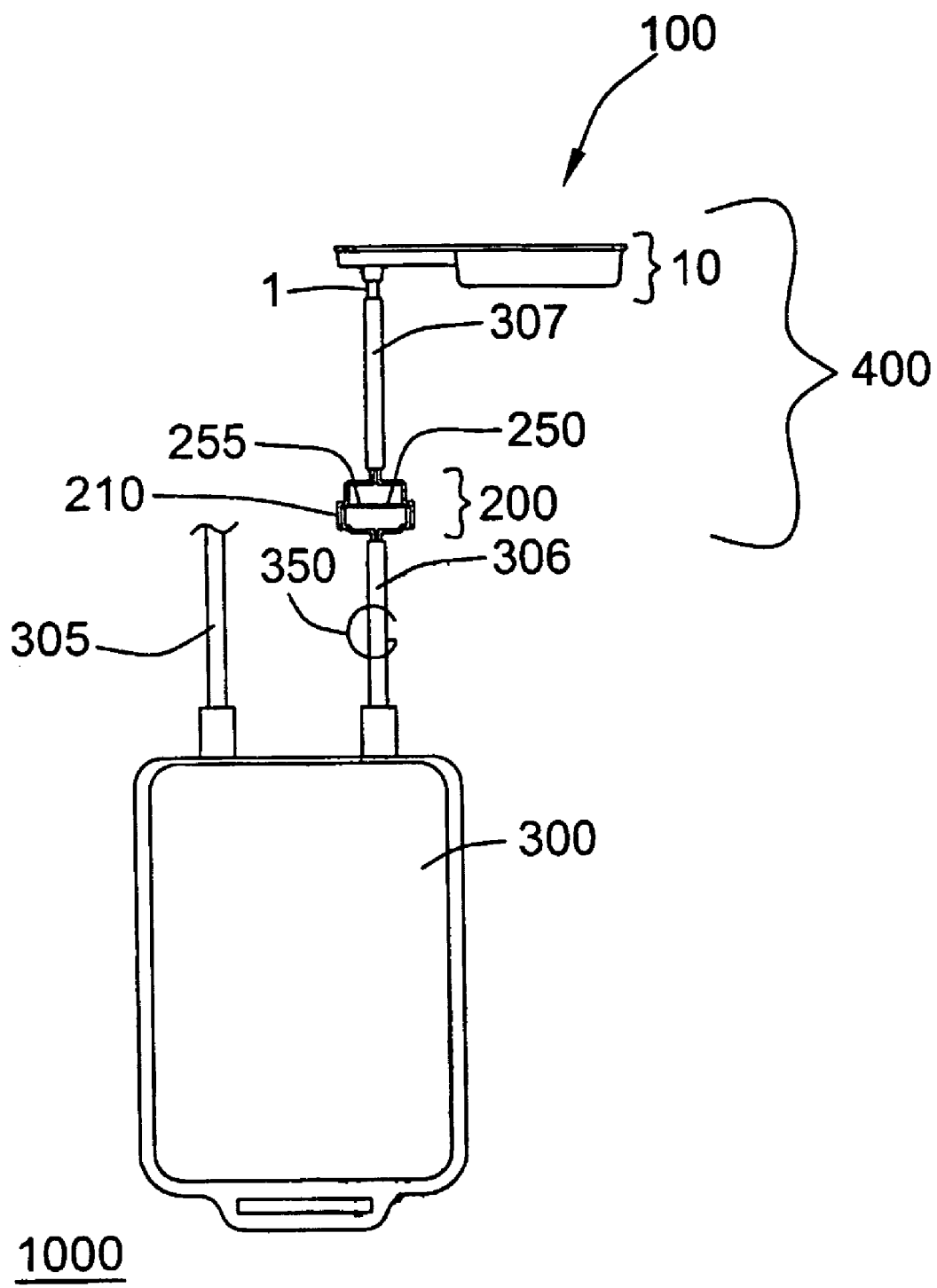
FIG. 9 illustrates an embodiment of a biological fluid processing system according to the invention, showing a first container for holding a biological fluid, a processing arrangement including a filter assembly and a biological fluid analysis device, wherein the filter assembly is interposed between, and is in fluid communication with, the first container and the analysis device.

FIG. 9 shows an embodiment of a biological fluid processing system 1000, comprising a biological fluid processing arrangement 400 including a biological fluid analysis device 100 and a filter assembly 200 comprising a filter housing 210, and a filter 250 comprising at least one filter element 255. In this illustrated embodiment, the system 1000 further comprises at least one container 300 (e.g., a source container) suitable for containing a biological fluid, a plurality of conduits 305, 306, and 307, and a flow control device 350.

Figure 10:
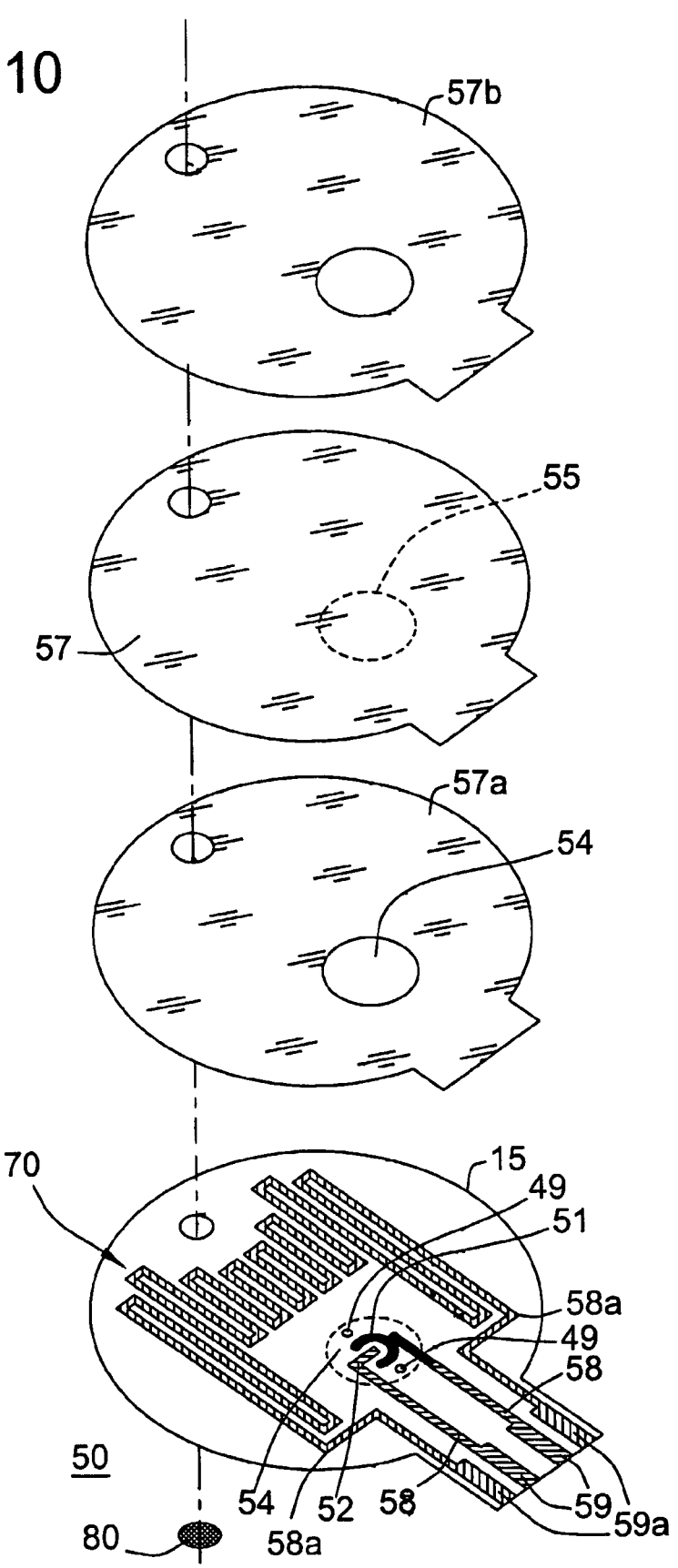
FIG. 10 shows another embodiment of a biosensor and a heater according to the invention, the biosensor including a working electrode, a reference electrode, an electrode chamber, an electrode cover, an insulator element, and a retaining element, wherein the biosensor and the heater are disposed on a support member.

FIG. 10 shows another embodiment of a biosensor 50, including the components shown in FIG. 1, wherein the biosensor further comprises a retaining element 57b covering the electrode cover 57, and the retaining element 57b is arranged so that it does not block or cover a portion of the electrode cover 57. FIG. 10 also shows the biosensor 50 and a heater 70 disposed on a support member 15.

In accordance with the invention, the biosensor is disposed to communicate with a biological fluid analysis chamber containing biological fluid possibly including microorganisms such that the oxygen concentration in the analysis chamber is detected, and, if microorganisms are present, the oxygen consumed by the microorganisms can be detected. More preferably, the biosensor monitors the oxygen consumed by bacteria in the analysis chamber over a desired period of time.

Using the embodiments illustrated in FIGS. 1 and 10 for reference, biosensor 50 comprises a working electrode 51, and a reference electrode 52 (each electrode further comprising a conductive trace 58 comprising a contact pad 59) wherein the non-contact pad ends of the electrodes are disposed in an electrode chamber 54, and the electrode chamber is covered with an electrode cover 57 comprising a gas permeable element 55 that allows oxygen to pass into the chamber.

In these embodiments, an insulator element 57a (with a cutout portion corresponding to the area of the gas permeable element 55) is interposed between the lower surface of the electrode cover 57 and the upper surface of the traces 58 of the electrodes 51 and 52. FIG. 10 also shows an optional retaining element 57b covering the upper surface of the electrode cover 57, wherein retaining element 57b also has a cutout portion corresponding to the area of gas permeable element 55. Viewing the cutout sections of insulator element 57a (FIGS. 1 and 10) as well as that of retaining element 57b (FIG. 10), a portion of the electrode cover 57 is not blocked or covered by the elements 57a and 57b, and this unblocked or uncovered portion of the electrode cover 57 forms the gas permeable element 55. In these illustrated embodiments, the biosensor 50 is disposed on support member 15.

The electrode chamber 54 includes the region between the lower surface of the gas permeable element 55 and the upper surface of the support member 15, and the electrode chamber contains the working electrode 51, and the reference electrode 52. Sealed in the electrode chamber 54 are an electrocatalytically active enzyme, preferably laccase (the enzyme can be disposed on the working electrode 51), as well as an electrolyte (for conductivity).

The working electrode 51 and reference electrode 52 are formed using conductive traces 58, preferably disposed on the support member 15. The conductive traces are typically formed using a conductive material such as carbon (e.g., graphite), a conductive polymer, a metal or alloy, or a metallic compound. Suitable conductive materials include, for example, conductive ink or paste. Suitable commercially available conductive inks are available from, for example, Ercon, Inc. (Wareham, Mass.), Metech, Inc. (Elverson, Pa.), E. I. du Pont de Nemours and Co. (Wilmington, Del.), Emca-Remex Products (Montgomeryville, Pa.), and MCA Services (Melbourn, England).

Typically, the conductive ink is applied as a semi-liquid or paste which contains particles of carbon, metal, alloy, or metallic compound, and a solvent or dispersant. After application of the conductive ink on the support, the solvent or dispersant evaporates to leave behind a solid mass of conductive material. In some embodiments, the conductive ink also contains a binder, e.g., to further bind the conductive material to the support.

The working electrode 51 comprises an electro-conductive highly dispersed material such as flat or dispersed carbon, graphite, carbon black, conductive dispersed pyrolytic products, conductive metal oxides, metal and metal powers, semiconductor materials, and dispersed conductive polymers.

The reference electrode 52 comprises an electro-conductive material such as silver (Ag), silver/silver chloride (Ag/

AgCl), mercury (Hg), mercury chloride (calomel) (e.g., the reference electrode can be a calomel reference electrode), or a non-leachable redox couple bound to a conductive material, for example, a carbon-bound redox couple.

In some embodiments, the electrodes are formed using conductive ink as described above with respect to the conductive traces. The ink(s) can include one or more binders. Suitable commercially available conductive inks include those described above.

Figure 6A:
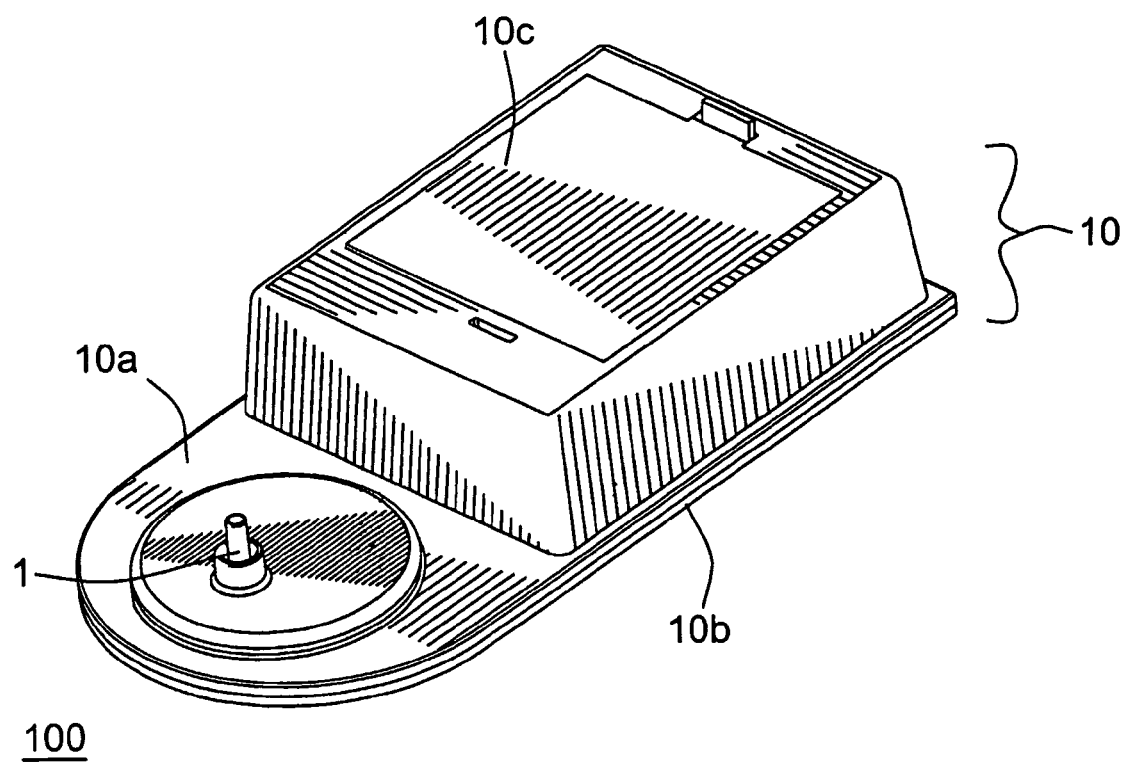
FIG. 6a shows a perspective view (with the battery cover inserted) of the assembled device.
Figure 6B:
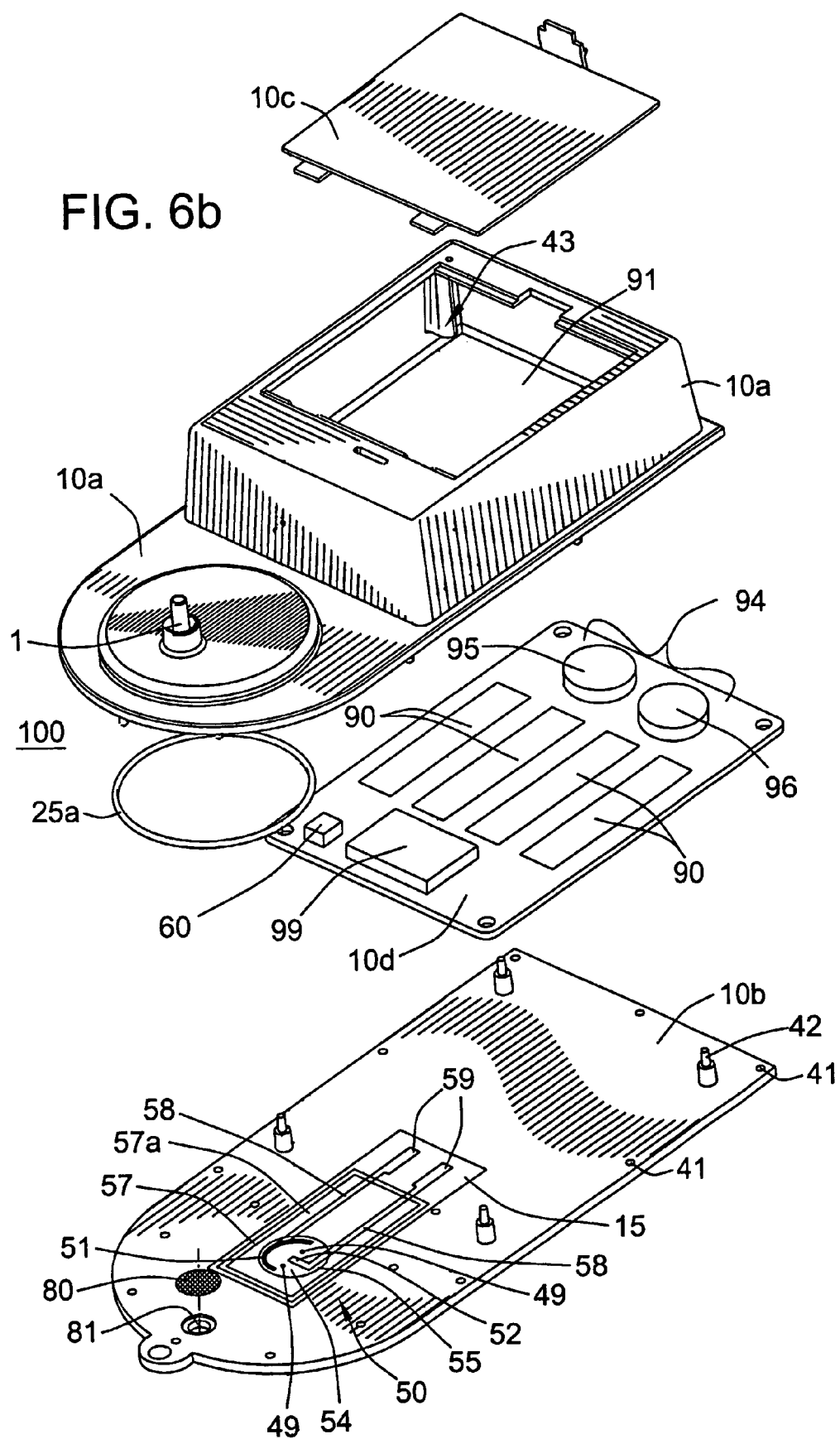
FIG. 6b shows an exploded view of the device also showing the biosensor.
Figure 6C:
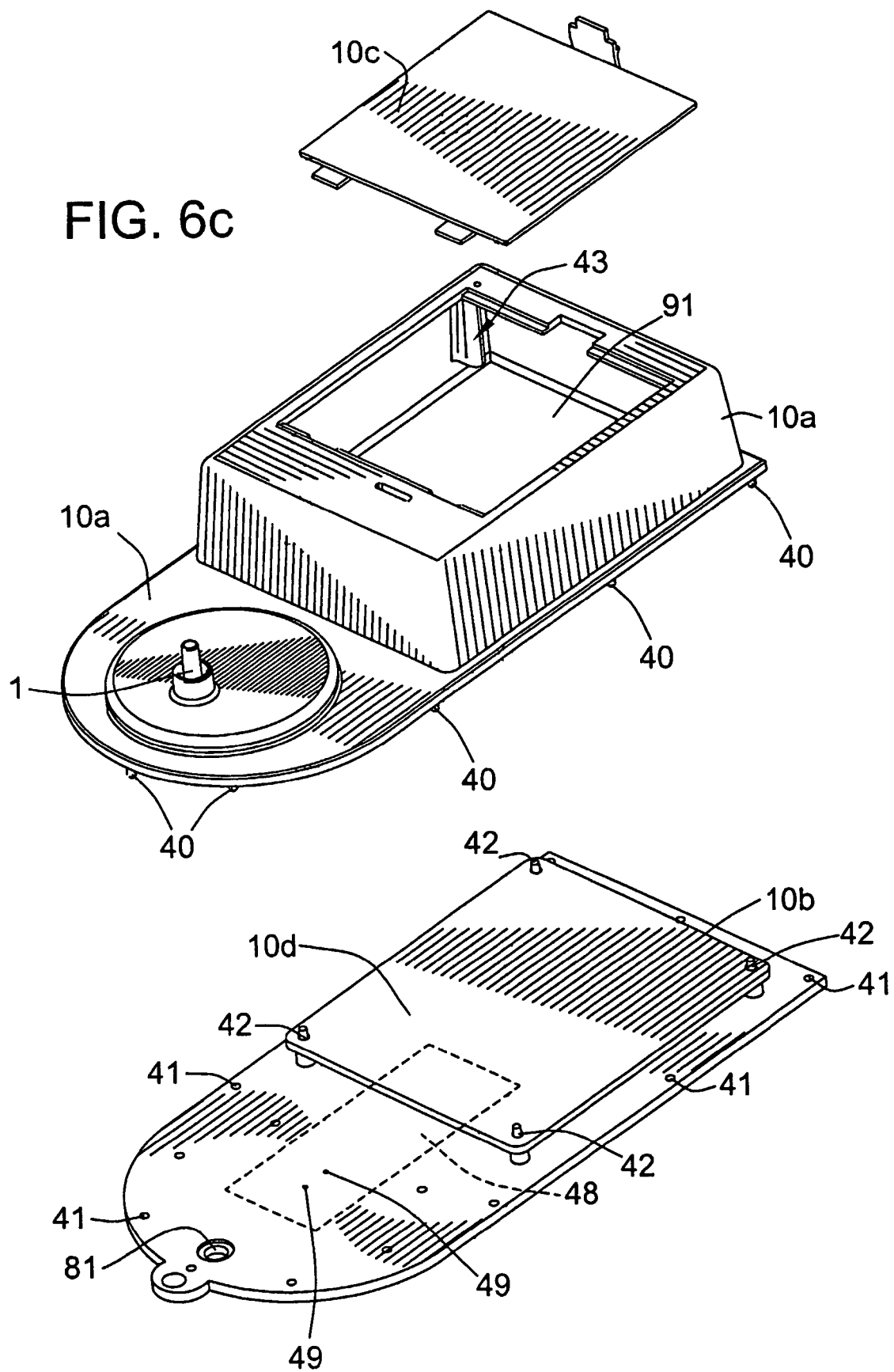
FIG. 6c shows an exploded view of the housing.
Figure 6D:
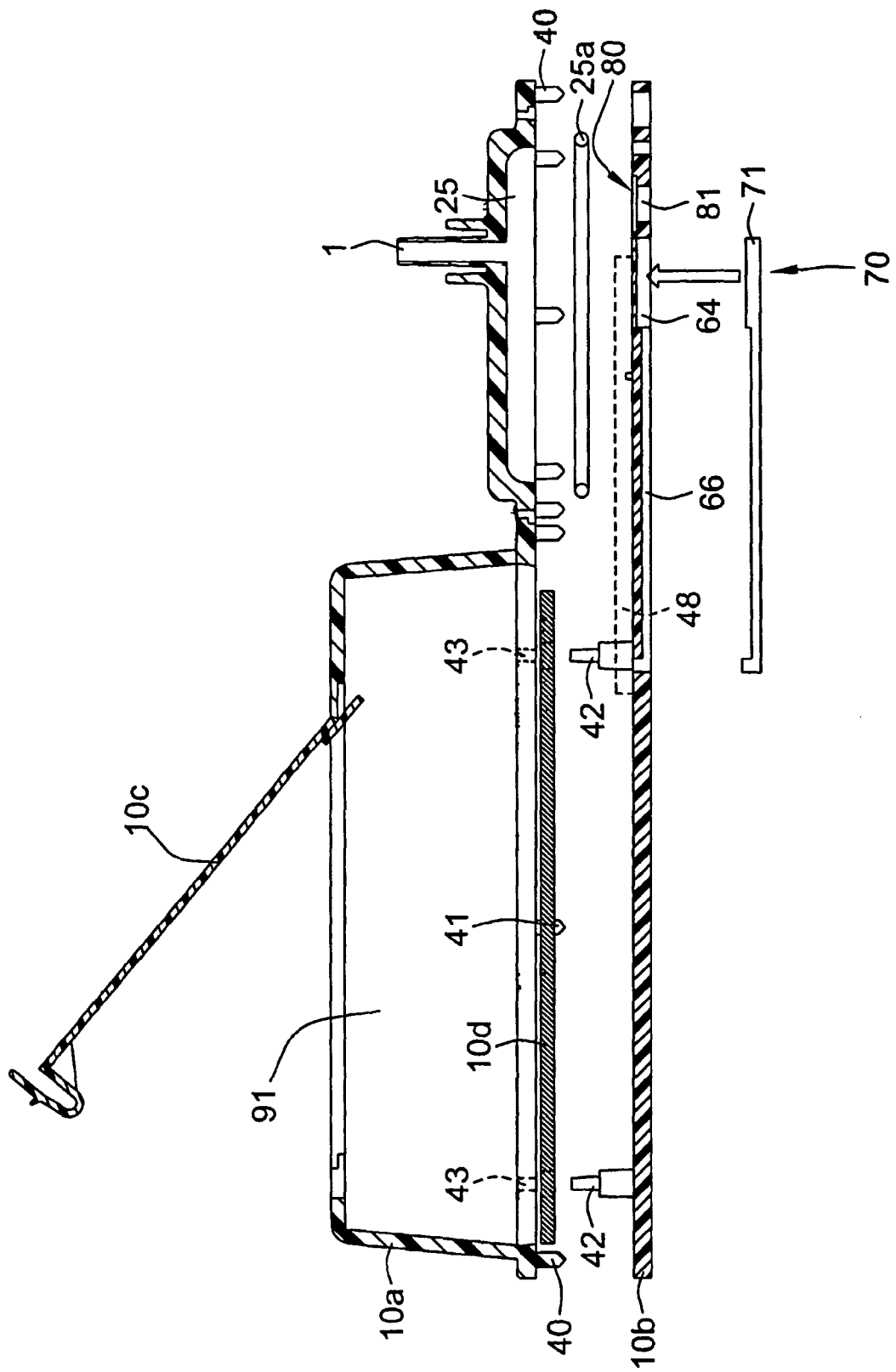
FIG. 6d shows a cross-sectional side view of the housing, as well as an analysis chamber seal and a heater.
Figure 6F:
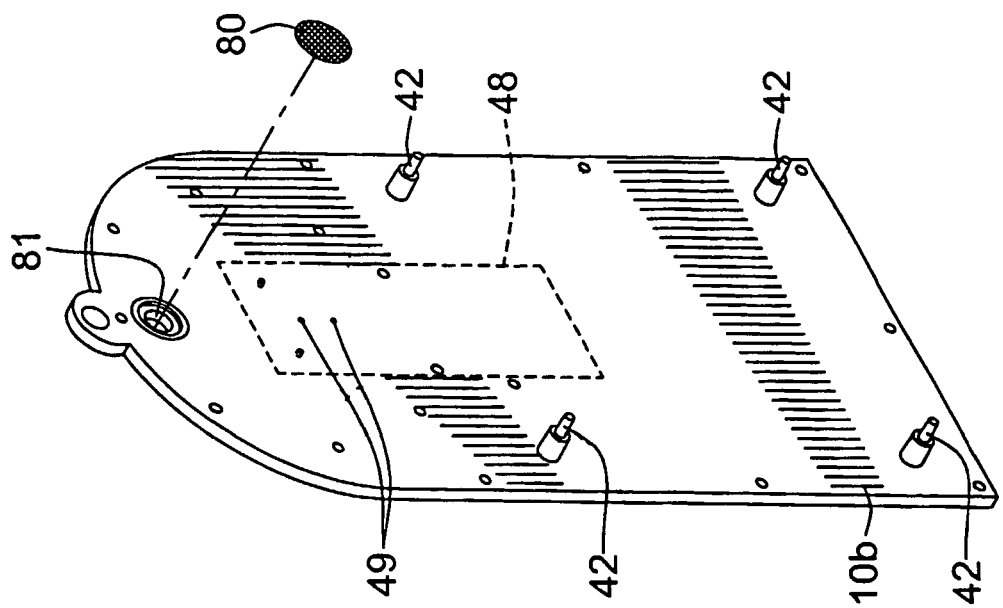
FIG. 6f shows a top view of the bottom section of the housing for receiving the biosensor.

The conductive traces and electrodes are adherently and securely deposited on the support member 15 (FIGS. 1, 2, 6b, and 10) or the housing (e.g., they can be deposited on housing section 10b, for example at region 48 shown in FIGS. 6c and 6f) as is known in the art, e.g., by vapor deposition (e.g., chemical vapor and physical vapor) sputtering, reactive sputtering, printing (e.g., silk screening), coating, painting, and electrolytic processes. In some embodiments, die cut electrodes of thin sheet form can be adhered to the housing or support member.

If desired, the traces and/or electrodes can be disposed in a cutout, depression, or groove in the support member or housing, for example, so that the top surface of the traces and electrodes is flush, or nearly flush, with the top surface of the non cut-out section of the support member or the housing. Such an arrangement can be suitable for some protocols for fluid tight sealing of the housing.

Turning back to FIGS. 1, 6b, and 10 for reference, a portion of each of the conductive traces 58 is typically suitable for contacting the conductive contacts of the processing unit 99 (the processing unit is described in more detail below), e.g., the traces can include contact pads 59. Each contact pad can be indistinguishable from the rest of the conductive trace, but more commonly (e.g., as shown in FIGS. 1, 6b, and 10) has a larger width than other regions of the trace to facilitate a connection with the contacts on the processing unit. The contact pad can be made using the same material as the conductive traces and/or electrodes, but this is not necessary.

As shown in FIGS. 1 and 10, the electrode cover 57, covering electrodes 51 and 52, comprises a gas permeable element 55, wherein the gas permeable element comprises a porous or semi-porous structure, preferably a membrane, that allows the gas to be detected (oxygen) to pass freely therethrough, but is essentially impermeable to bacteria, platelets, white blood cells, red blood cells, and molecular components of plasma. Accordingly, using FIG. 6b for reference, biological fluid passing into analysis device 100 through inlet 1 into analysis chamber 25 contacts the electrode cover 57 (including the gas permeable element 55), but the biological fluid does not pass through the cover and contact the enzyme or the electrodes in the electrode chamber 54.

The gas permeable element 55 shown in FIGS. 1, 6b, and 10 is hydrophobic, either as formed, or due to post formation treatment or modification. Suitable electrode covers and gas permeable elements comprise, for example, polypropylene, or more preferably, polyethylene (e.g., polytetrafluoroethylene (PTFE)) membranes, and are commercially available.

The electrode cover 57 can include additional elements or components, or, more preferably, additional elements or components can be placed in contact with the cover 57, e.g., as shown in FIGS. 1 and 10.

For example, in some embodiments an insulator element such as at least one non-conductive layer or film, e.g., a polyester, plastic, or other suitable polymeric film, preferably an adhesive-backed or thermally sealable film (suitable films are commercially available, and are known to the skilled artisan), is interposed between the lower surface of the electrode cover 57 and the upper surface of conductive traces 58. Illustratively, using FIGS. 1, 2, 6b, 10 and 11 for reference, an insulator element 57a comprising a film having adhesive on both sides and a cut out area to be located over the non-contact pad ends of the electrodes 51 and 52 (e.g., to form the side walls of the electrode chamber 54 while keeping the gas permeable element 55 uncovered) can be adhesively mounted to the lower surface of the electrode cover 57, as well as the upper surfaces of conductive traces 58 and the support member 15. The portion of the electrode cover 57 not blocked by the insulator element 57a provides the gas permeable element 55, while covering the ends of the electrodes and sealing the electrode chamber 54. The insulator element minimizes or prevents the loss or degradation of signal caused by unwanted electrical pathways from one electrode to another. With respect to devices including a heater (e.g., as shown in FIG. 10), in addition to reducing heat loss and/or spreading the heat evenly, in some embodiments, the insulator element electrically isolates the heater from the electrode chamber.

FIG. 10 also shows an optional retaining element 57b (that can comprise a film, preferably an adhesive-backed or-thermally sealable film, that can be similar or identical to insulator element 57a as described above; suitable films are commercially available, and are known to the skilled artisan) mounted to the upper surface of the electrode cover 57. In some embodiments, the use of a retaining element keeps the electrode cover in a desired position and/or location. Alternatively, or additionally, the retaining element can keep the electrode cover, especially the gas permeable element, substantially flat.

The electrode chamber 54 (also shown in cross-sectional views in FIGS. 4a, and 4b) contains the enzyme and an electrolyte (for conductivity) therein. If desired, the electrode chamber can further comprise a nonconductive cup sealed to the electrode cover 57 and around the ends of the working and reference electrodes. Alternatively, or additionally, the support member or the bottom section of the housing can include or provide a depression such as a groove, cutout, or cavity having the ends of the electrodes arranged therein, such that the electrode cover 57 comprising gas permeable element 55 can be sealed over the depression to provide the electrode chamber. Illustratively, FIGS. 4a and 4b show a depression in a portion of housing section 10b, wherein support member 15 comprises a flexible film that generally follows the contours of the depression and forms a portion of the electrode chamber 54. However, the depression is not required, and the embodiment illustrated in FIG. 6b does not include such a depression. In all of these embodiments, the electrode chamber is sealed such that oxygen can enter the chamber, but bacteria and components of the biological fluid, e.g., platelets, white blood cells, red blood cells, and molecular components of plasma, do not enter the electrode chamber.

Since the electrode cover 57 allows oxygen to pass therethrough, but is essentially impermeable to bacteria and the components of the biological fluid, the oxygen diffusing through the cover will contact the enzyme essentially free of interfering material or interfering substances.

The enzyme (preferably laccase) is free to migrate in the electrolyte and contact the electrodes. In some embodiments, the enzyme is applied to the working electrode during the assembly of the analysis device. The electrolyte, that can comprise a liquid, a gel, or a sol-gel matrix, includes a buffer solution, preferably containing a source of chloride and sodium ions. Suitable buffer solutions include, but are not limited to, buffered saline (e.g., borate-, acetate-, and phosphate-buffered saline), and Good's buffer (e.g., MES). The electrolyte can also include detergents, such as, but not limited to, Tween, and Triton, as well as organic compounds such as N,N'-dimethyl formamide.

The biosensor 50 (FIGS. 1 and 10) can be disposed in a biological fluid analysis housing in a variety of suitable arrangements and/or orientations. For example, the biosensor 50 can be directly mounted to the biological fluid analysis device housing, e.g., at region 48 in housing section 10b in FIGS. 6c and 6d. Typically, however, the biosensor is mounted to a support member 15 as shown in FIGS. 1, 2, 6b, 10 and 11. In an embodiment, support member 15, that is preferably planar, comprises a nonconductive or insulative element such as a film and/or a circuit board card such as a glass (including fiberglass) or polymeric (e.g., plastic) substrate. The support member 15 can be similar or identical to the insulator element 57a. The support member can comprise a laminate or composite, e.g., a film adhered to a plastic element. In addition to glass, suitable materials include, for example, phenolic materials, and thermoplastics such as polycarbonates, polyesters, polyvinyl chloride, polyurethanes, polyethers, polyamides, polyimides, and copolymers of these materials. Suitable support members are commercially available, and are known to the skilled artisan.

As shown in FIG. 2, one embodiment of a biological fluid analysis device 100 comprises a housing 10 having a first section 10a and a second section 10b, the housing including a biological fluid analysis chamber 25 having an internal volume suitable for receiving a plasma-containing portion of biological fluid, an inlet port 1 and a vent 80, both in fluid communication with the analysis chamber 25; the biosensor 50 (as described above); a power source 90 comprising at least one battery; a high input impedance amplifier 60; an analog-to-digital (A/D) converter 65; a processing unit 99, and a signal generator such as a visible marker 94 comprising two indicator lamps 95 and 96, disposed on a support member 15 suitable for mounting the biosensor, power source, processing unit and indicator lamps thereon. In this illustrated embodiment, the first housing portion 10a includes a chamber 91 for containing the power source 90 and the processing unit 99, and chambers 95a and 96a for containing the indicator lamps 95 and 96, respectively. First housing portion 10a also includes wall 11 separating the chamber 91 from the analysis chamber 25, and wall 12 separating the chamber 91 from the chambers 95a and 96a.

In the embodiment shown in more detail in FIG. 6b, the biological fluid analysis device 100 comprises a housing 10 having a first section 10a, a second section 10b, and a third section 10c, the housing including a biological fluid analysis chamber 25 having an internal volume suitable for receiving a plasma-containing portion of biological fluid, an inlet port 1, a vent 80 and a vent port 81, in fluid communication with the analysis chamber 25, and a biosensor 50 disposed on a support member 15. As shown in FIGS. 6b and 6c, in this embodiment the housing 10 also includes a fourth section 10d (e.g., an additional support member), and the power source 90 comprising at least one battery, the high input impedance amplifier 60, the processing unit 99, and the visible marker 94 comprising two indicator lamps 95 and 96 are disposed on the additional support member 10d.

The housing 10, as well as the various chambers (especially analysis chamber 25), and the inlet port 1, can have any suitable size and/or configuration (e.g., shape), and can be fabricated from any suitably rigid, impervious material, including any impervious thermoplastic material, which is compatible with the biological fluid being processed. In an embodiment, the housing is fabricated by injection molding from a polymer, more preferably a transparent or translucent polymer, such as an acrylic, polypropylene, polystyrene, or a polycarbonate resin. Not only is such a housing easily and economically fabricated, but it also allows observation of the liquid (and the other components of the device) in the housing.

Typically, the housing 10 comprises a plurality of sections or portions that are assembled and sealed together. For example, in the embodiment shown in FIGS. 2 and 3, the device comprises a first section 10a and a second section 10b, that are subsequent sealed together as shown in FIGS. 4a, 4b, and 8c, and in the exemplary embodiment shown in FIGS. 6a14 6g, the device comprises a first section 10a, a second section 10b that are subsequently sealed together, and the housing further comprises at least a third section 10c (e.g., a battery cover) that is assembled with the first section 10a. As will be described below, and as shown in FIG. 6b, the housing can comprise additional components, e.g., one or more pins 40 (shown in more detail in FIGS. 6d and 6f) and corresponding cavities or holes 41 (shown in more detail in FIG. 6e) for aligning sections of the housing. FIG. 6b also shows another set of pins 42 and corresponding cavities or holes 43 (shown in more detail in FIGS. 6f and 6g) for aligning sections of the housing, e.g., the chamber for containing the power source and the additional support member 10d (shown in FIGS. 6b–6d).

Once assembled, e.g., as shown in FIGS. 6a and 8a, the biological fluid analysis device 100 (especially the analysis fluid chamber) preferably has a liquid-tight seal with the exception that inlet port 1 allows fluid communication with the analysis chamber 25, and the battery cover 10c or tab need not be hermetically sealed to the other sections of the housing. The housing can be sealed as is known in the art, e.g., using at least one of an adhesive, a solvent, radio frequency sealing, ultrasonic sealing, heat sealing, staking and/or crimping. In the embodiment illustrated in FIGS. 6b, 6d and 6g, the device 100 includes analysis chamber seal 25a such as a gasket or an O-ring, typically made from materials such as rubber, silicone, and styrene.

In an embodiment, the device 100 (e.g., the analysis chamber 25) includes at least one reagent, solution, additive, growth medium and/or culture medium therein, e.g., to prevent a lag in growth of the microorganisms and/or to improve the growth rate. In some embodiments, minimizing the lag in growth and/or improving the growth rate allows the microorganisms to be detected more quickly. A variety of reagents, solutions, additives, growth media and/or culture media are suitable. They can be in dry form (e.g., a powder or a "tablet," that typically also includes an inert material such as at least one of maltose and mannitol to provide bulk) or liquid form. In one embodiment, the analysis chamber includes sodium polyanethol sulfonate (SPS) in dry or liquid form.

Figure 6E:
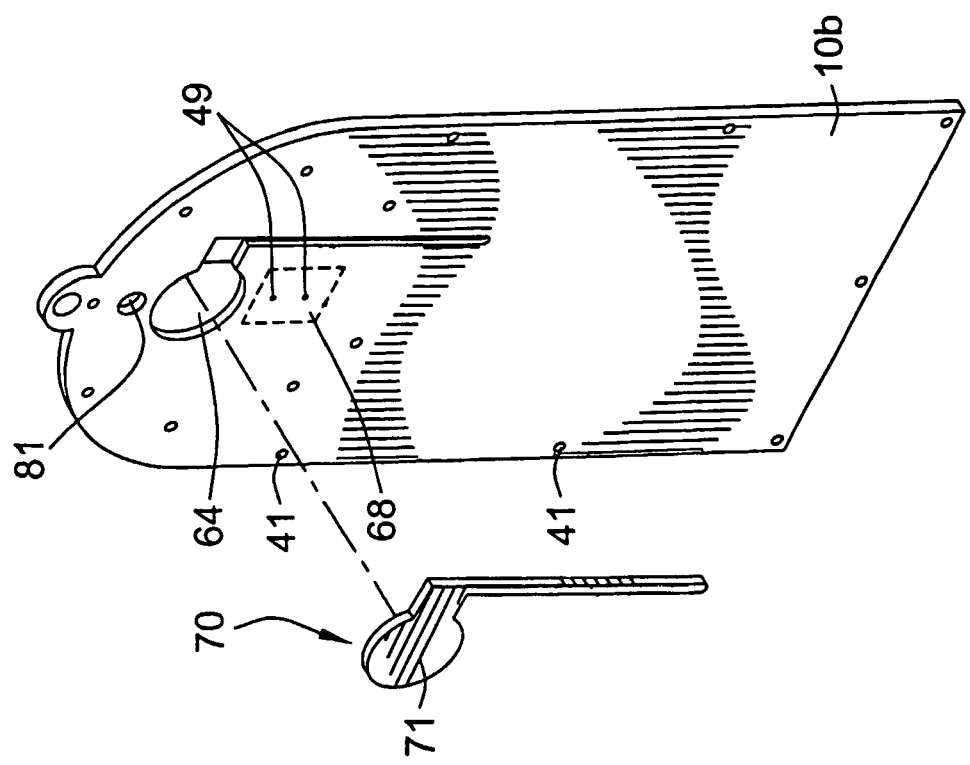
FIG. 6e shows a bottom view of the bottom section of the housing for receiving the heater.
Figure 6G:
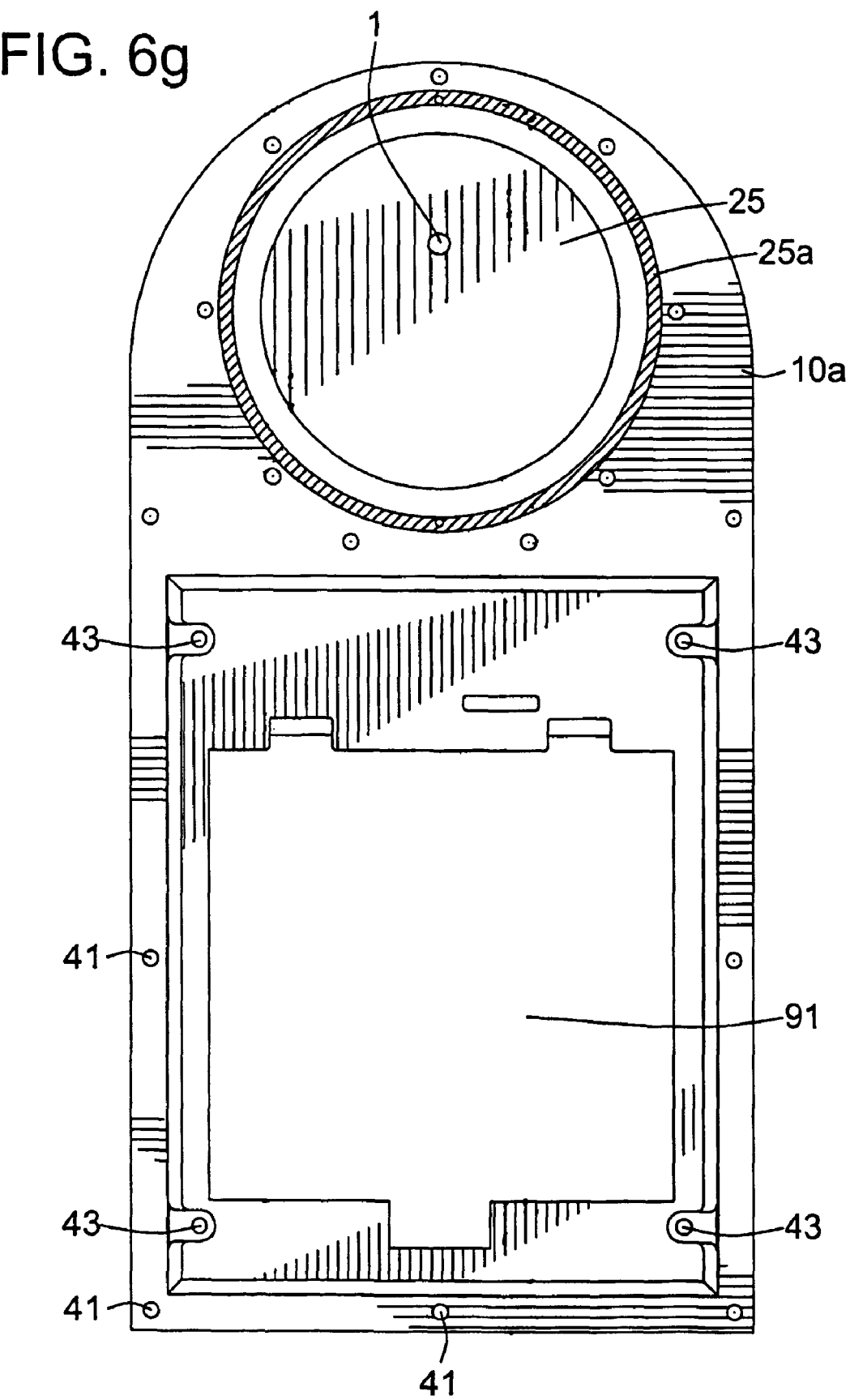
FIG. 6g shows a bottom view of the top section of the housing, including the analysis chamber.

If desired, e.g., as shown in FIGS. 6b, 6d, and 6g (as described above), the housing can include pins 40 and cavities or holes 41, as wells as pins 42 and cavities or holes 43, for aligning the sections of the housing during assembly and for ease of sealing the housing.

In some embodiments, the housing 10 includes one or more access portions, such as sealable openings, communicating with the electrode chamber 54, e.g., to allow introduction of the solution containing the enzyme into the chamber after the housing portions are assembled. Illustratively, and using the embodiments shown in FIGS. 6b, 6c, 6e, and 6f for reference, the housing portion 10b can include one or more openings such as at least two holes 49 and these holes can extend through the portion 10b into the electrode chamber 54 (shown in more detail in FIG. 6b; holes 49 also shown in FIG. 10), without the holes passing through the electrodes 51, 52 or the electrode cover 57. Alternatively, using the embodiment shown in FIG. 2 for reference, the housing portion 10b can include two holes and these holes can extend through support member 15 (holes not shown in the support member) into the electrode chamber without passing through the electrodes or the electrode cover. These arrangements allow the enzyme containing solution to be introduced through one opening into the electrode chamber 54 while displacing air through the other opening. Once the electrode chamber contains the desired solution, the openings can be sealed by any suitable technique as is known in the art, e.g., using a gas impermeable or essentially impermeable film or membrane with an adhesive backing allowing the impermeable material to be adhered to the housing, e.g., at region 68 (FIG. 6e).

Using FIGS. 6a, 6b, and 8a for reference, the inlet port 1 typically comprises a fitting or connector, such as a luer connector. In some embodiments, e.g., wherein the device 100 is supplied as a separate unit, rather than being pre-attached to another element of a biological fluid processing system such as a filter assembly or conduit, the inlet port 1 is configured to receive a cap or cover. For example, the cap or cover can be utilized to maintain sterility of the device before use.

As noted above, the analysis chamber 25, that receives the biological fluid via the inlet port 1, can have any suitable size and/or configuration. Typically, the chamber has an internal volume of at least about 2 ml, and in some embodiments, in the range of from about 5 ml to about 50 ml, or more. Since as shown in, for example, FIGS. 3 and 6b, the device 100 preferably also includes a vent 80 (described below) communicating with the analysis chamber, the biological fluid entering the analysis chamber displaces gas (e.g., air) from the chamber, allowing the internal volume of the chamber to be filled, or substantially filled, with the biological fluid. However, the biosensor will function with a portion of air remaining in the analysis chamber.

The device 100 and the analysis chamber 25 are arranged to allow the biosensor 50 to be positioned to detect the oxygen concentration in the chamber over a desired period of time. Illustratively, FIG. 3 (showing an exploded internal view of an embodiment of the device), and FIGS. 4a and 4b (showing various cross-sectional views of an assembled device) show biosensor 50 extending into a portion of the internal volume of the analysis chamber 25. Once the housing 10 is assembled and the analysis chamber is filled with biological fluid, biological fluid contacts the electrode cover 57 but does not pass through the gas permeable element 55. However, oxygen diffuses from biological fluid in the analysis chamber through the gas permeable element 55 into the electrode chamber 54 containing the enzyme. Since microorganisms (if present in the biological fluid) consume oxygen, the biosensor 50, exposed to a decreased concentration of oxygen, exhibits an observable decrease in electrode potential, and the voltage drop is approximately proportional to the decrease in oxygen concentration.

In the illustrated embodiments shown in FIGS. 2, 3, 4a, 4b, 6b, and 8b, the device 100 includes at least one vent 80 (liquid-tightly sealed to the housing 10 and communicating with the analysis chamber 25 via vent port 81), comprising at least one microporous membrane, the membrane having a bacteria blocking pore structure such as a bacteria blocking pore rating. The vent 80 can be disposed in a variety of locations, e.g., attached to the housing as described above, and/or attached to another component of the biosensor, e.g., the support member, or the insulator element. The use of a vent efficiently allows the displacement of air from the device (i.e., from the analysis chamber and through the microporous membrane) as biological fluid passes into the device, while preventing bacteria from the outside environment from passing through the vent into the device. Since air is displaced from the device, the device can be filled more completely, and, since a greater volume of biological fluid sample is present, can allow the microorganisms to be detected more quickly. If desired, after the device is filled with biological fluid, the vent can be sealed or closed by techniques known in the art (e.g., by covering the vent with a gas impermeable material). For example, the vent can be sealed to prevent external air from diffusing through the vent into the device. While the device will function with air present in the analysis chamber, the biosensor may equilibrate more quickly if the presence of air in the analysis chamber is minimized.

Preferably, the microporous membrane includes at least a liquophobic layer or element, and can also include at least one liquophilic layer or element, e.g., to seal the vent once the liquophilic layer or element is contacted by the biological fluid. Suitable vents include, but are not limited to, those disclosed in U.S. Pat. Nos. 5,126,054; 5,451,321; 5,863,436; 5,364,526; and 5,472,621, and International Publication No. WO 91/17809.

Typically, the housing includes at least one chamber for receiving at least one other component of the device. For example, FIGS. 2 and 3 show device 100 including chambers for receiving power supply 90 and processing unit 99 (chamber 91; also shown in FIG. 4b), indicator lamp 95 (chamber 95a) and indicator lamp 96 (chamber 96a). In other embodiments (e.g., FIG. 6b), a single chamber 91 receives each of the components, or the device can have other arrangements of chambers.

For example, the analysis device can have a single chamber for a single signal generator that is capable of emitting a variety of distinguishable signals (e.g., different colors), or a single chamber can be used for at least two signaling elements, e.g., two or more indicator lamps and/or acoustic devices (not shown). In desired, one or more chambers for receiving at least one indicator lamp and/or for receiving at least one acoustic device can be arranged to more efficiently transmit the indicator signal. Additionally, or alternatively, the lamp and/or acoustic device can be arranged to more efficiently transmit the indicator signal. For example, the indicator lamp and/or a chamber can include a portion that reflects and/or magnifies the signal.

The housing can include additional structures or elements, such as, but not limited to, a plurality of interior walls, e.g., walls 11 and 12 as shown in FIGS. 2 and 3. Alternatively or additionally, the housing can include one or more movable elements (not shown), e.g., a movable wall acting as a valve to prevent fluid communication between the inlet port and the analysis chamber after the analysis chamber has been filled with biological fluid. Typically, the housing also includes a removable section 10c, e.g., a replaceable cover or tab to allow the battery to be inserted and/or discarded.

The power source 90 (FIGS. 3, 5, 6b, and 7) provides power to operate the high input impedance amplifier (the amplifier providing an amplification of the potential from the electrodes of the biosensor 50), the processing unit 99 (containing the algorithm for analyzing measurements from the electrodes), the visible marker 94, and other components. As shown in the block diagram in FIG. 5, the power source 90 provides power to operate the high input impedance amplifier 60, the analog-to-digital (A/D) converter 65, the processing unit 99, and the signal generator, e.g., the visible marker 94. In the embodiment illustrated in FIG. 7, the power source 90 provides power to operate the high input impedance amplifier 60, the processing unit 99, the signal generator, e.g., visible marker 94, and the heater 70 (comprising a thermistor 71).

The power source 90 is preferably self-contained, e.g., one or more disposable batteries or cells (the embodiment illustrated in FIG. 6b has 4 batteries). The power source typically has a shelf-life of at least about 12 months, preferably, a shelf-life of about 2 years or more, and in some embodiments, a shelf-life about 5 years, or more. A variety of commercially available power sources are suitable, including, for example, one or more 1.5, 3, 6 and/or 12 volt batteries (e.g., lithium batteries) conventionally used for hearing aids, watches, cameras, flashlights, and the like. In some embodiments, carbon-based batteries or certain classes of lithium batteries (that can be conventionally disposed of in a more environmentally benign manner, e.g., without special handling) are utilized. In some embodiments, the biological analysis device is arranged so that the power source can be inserted into the housing, or discarded, when desired, e.g. just before use and/or after use.

In some embodiments, the power source comprises one or more rechargeable batteries. For example, a plurality of analysis devices can include similar plugs and/or wiring harnesses allowing two or more devices to be recharged at a "docking station" essentially simultaneously.

The processing unit 99 (FIGS. 3, 5, 6b, and 7) analyzes the measurements from the biosensor, and tracks the changes in potential over time. The processing unit preferably comprises a microprocessor, although in some embodiments it can comprise a microcontroller. The microprocessor can also include, for example, a high input impedance amplifier, and an analog-to-digital (A/D) converter (or the microprocessor can run A/D converter software).

A variety of suitable microprocessors and microcontrollers are commercially available. Typically, the microprocessor has low voltage operation (e.g., in the range of from about 2.5 to about 5.5 vdc), power savings modes, 8 bit operation, at least 16 KB internal ROM and at least 512 Bytes internal RAM.

A variety of suitable high input impedance amplifiers, analog-to-digital (A/D) converters, and A/D converter software are also commercially available. Typically, the amplifier and converter have single power supply operation (e.g., in the range of from about 2.5 to about 5.5 vdc) and low power operation (e.g., about 100 μa, or less).

The power source and the processing unit can be arranged at any desired location(s), e.g., in or on the housing.

Preferably, the processing unit 99 monitors and/or interprets the level or rate of change of the electrode potential, and, using for example, a suitable algorithm, compares the value to a preset or computed reference, threshold value and/or other parameter as established by a separate or integral portion of the algorithm. When the change reaches, for example, a total change of about 10 mV or more for three successive measurements (e.g., three successive measurements of about 3 mV each), a signal is generated, e.g., an acoustic device or a visible marker (e.g., a indicator lamp) is activated. Alternatively, or additionally, the change leading to a generated signal can be an increase in the rate of change, for example, greater than about 4% decrease for two successive measurements.

A variety of protocols are suitable for monitoring and/or interpreting the level or rate of change of the electrode potential and comparing the value to a preset reference, threshold value and/or algorithm, e.g., to activate the visible marker indicating a clinically significant level of microorganisms (preferably bacteria) is present. For example, a number of commercially available software programs (e.g., ORIGIN®, including versions 3.5, 5.0 and 6.1 (OriginLab Corporation, Northampton, Mass.)), reference books (e.g., Documenta Geigy: Scientific Tables, Ciba-Geigy Ltd., for example, 7th Edition, (Diems and Lentner, eds., 1972)) and textbooks provide a variety of suitable algorithms (including smoothing algorithms) as is known in the art. With respect to algorithms, while using a first derivative (the slope of the curve) is suitable for carrying out the invention, using a second derivative (the rate of change of the slope of the curve) and monitoring when the second derivative has a value of zero allows the clinically significant level of microorganisms to be determined more rapidly. For example, in one embodiment, once the second derivative has a value of zero, the signal generator is activated to emit a signal indicating a clinically significant level of microorganisms is present.

In accordance with the illustrated embodiments (e.g., FIGS. 3 and 6b, and shown in the block diagrams in FIGS. 5 and 7), the processing unit 99 activates a signal generator such as visible marker 94 including a plurality of elements, e.g., a first indicator lamp 95 to show that the level or rate of change is being monitored and has not reached (e.g., within a predetermined period of time) the preset reference, threshold value and/or algorithm calculation, and a second indicator lamp 96 to show the level or rate of change has reached the reference value, threshold value and/or algorithm calculation.

The signal generator can have any suitable number of signaling elements (e.g., providing visual and/or acoustic signals) and/or the signal generator can be capable of producing a variety of distinguishable signals to provide desired information over any desired period of time. For example, the signal generator can be arranged to provide a signal, via a different element, a combination of elements, or an element capable of emitting a variety of distinguishable signals, during and/or after each day of biological fluid storage, to provide one or more parameters of interest. Illustratively, one signal element can be activated after a first day of storage to indicate a clinically significant level of bacteria is not present within a predetermined period of time, another signal element can be activated after the second day, and so on. If, for example, a clinically significant level of bacteria is detected during another day of storage, a signal element that is preferably readily distinguishable from the other elements is activated. If desired, one or more other signal elements can be arranged to indicate any other parameter of interest, e.g., to show the level or rate of change is still being monitored. In another embodiment, a signal is generated and transmitted to another location, e.g., via an infrared port.

Typically, the processing unit controls (via software) one or more drivers (e.g., switch transistors or relays) that activate the signal generator(s), e.g., turn the visible marker(s) or acoustic device(s) on and off. If desired, one or more lamps can remain on continuously, or flash on and off. In an embodiment, one indicator lamp or acoustic device is turned off and remains off when the second indicator lamp or acoustic device is turned on. In a preferred embodiment, the signal generator is arranged such that the activation of the lamp(s) and/or acoustic devices (s) notifies the technician that the biological fluid in the device contains a clinically significant level of bacteria (and thus, the biological fluid is the source container is not to be transfused) or the biological fluid does not contain a clinically significant level of bacteria (and thus, the biological fluid can be transfused).

The signal generator(s), e.g., marker(s) and/or acoustic devices, can be arranged at any desired location(s), e.g., in or on the housing, and suitable signal generators are commercially available and known to the skilled artisan. A variety of suitable visible markers, e.g., liquid crystal displays (LCDs), and indicator lamps such as colored lights or light emitting diodes (LEDs), as well as acoustic devices such as, for example, audible signal devices, e.g., solid state or piezo-electric crystal based devices, including audio transducers (e.g., conventionally used in, for example, watch alarms, smoke detectors and gas detectors), are commercially available. Preferably, the markers and/or acoustic devices have low current requirements, e.g., the indicator lamps and acoustic devices are low current lamps and devices, and more preferably, each has a different visible wavelength, or frequency. In a typical embodiment, at least one indicator lamp comprises an LED having an intensity of at least 500 mcd. More preferably, at least two such LEDs are utilized, each having a different visible wavelength.

The analysis device 100, and especially the processing unit 99, can have additional components such as, for example, one or more resistors, transistors and/or capacitors to complete the circuit.

In the embodiment of the block diagram shown in FIG. 7, a low drop-out voltage regulator 92 is interposed between the power source 90 and the processing unit 99 to provide stable voltage to operate the microprocessor even when the battery is weak, and a power interrupt 93 is interposed between the high impedance amplifier 60 and the processing unit 99 to provide additional control of power consumption by turning off the high impedance amplifier between readings (i.e., conserving power when readings are not being taken).

In some embodiments, the device further comprises a heater suitable for raising the temperature of the plasma-containing fluid in the chamber over the ambient temperature, preferably for a desired period of time. Illustratively, the heater, which comprises a thermally emitting element that is radiantly and/or conductively emissive (the heater can comprise, for example, at least one of a thermistor, a resistor, a lamp such as an incandescent lamp or light bulb, a disc- or foil-type heating element, a conductive trace, and a semiconductor), can be activated to raise the temperature from about 22° C. to about 35° C. for at least about 2 hours (typically, for at least about 4 hours, and in some embodiments, for at least about 6 hours, or more, e.g., at least about 12 hours, at least about 24 hours, at least about 36 hours, in some embodiments, for at least about 48 hours, or more), and/or can be activated to maintain the temperature in the range of from about 30° C. to about 37° C. (in some embodiments, in the range of from 32° C. to 35° C.) for these time periods.

Illustratively, using FIG. 7 for reference, the heater 70 (in this embodiment comprising a thermistor 71; the heater comprising a conductive trace shown in FIG. 10 can be similarly controlled) is turned on and off by a heater driver 75, that is controlled by the software in the processing unit 99, and the operation of the heater can continue for any desired period of time. The duty cycle of the heater can be varied, and the variation can be controlled by the software to sustain the desired temperature. In some embodiments, the heater (that can be self-regulated) can raise the temperature to a desired value or range within about one hour.

If desired, the activation of the heater can be interrupted any number of times, e.g., the power to the heater can be turned off when, for example, measurements are being taken from the biosensor and/or when it is desirable to conserve power. Illustratively, after the measurements are taken, the heater receives power until the next measurements are taken.

The heater can be disposed with respect to the biological fluid analysis housing in a variety of suitable arrangements and orientations while providing a sufficient internal volume for the biological fluid. The heater can be disposed internally within the analysis chamber or outside of the chamber. For example, the heating element of the heater can be in the form of an immersion heater extending into the internal volume of the analysis chamber, it can be in the form of a print or trace between a support and the insulator element, or the heating element can be in the form of a disk or plate mounted to a wall of the analysis chamber, or can be mounted to another portion of the housing.

Illustratively, using the embodiment illustrated in FIGS. 6d and 6e for reference, the heater 70 can be mounted outside of the analysis chamber 25, i.e., mounted to housing portion 10b in cutout portion 64, and the leads can be mounted in cutout portion 66. In the embodiment shown in FIG. 10, the heater 70 is mounted on support 15 (e.g., peripheral to electrodes 51 and 52), and covered by insulator element 57a. Alternatively, e.g., wherein the heater comprises an immersion heater or a light bulb or lamp, the "dome" of the bulb or lamp, or the immersion heater, can extend into the cavity of the chamber such that the plasma is heated upon contact with the dome or heater. In preferred embodiments, the heater is arranged such that the total energy output needed to increase the temperature of the plasma to a desired value can be reduced, allowing a smaller power source to be utilized.

A variety of suitable heaters are known in the art, and are commercially available. In typical embodiments wherein the heater comprises a thermistor or a conductive trace, the total energy output utilized to maintain a temperature of the biological fluid in the chamber in the range of from about 32° C. to about 35° C. for about 24 hours is in the range of from about 0.08 to about 0.4 Watts, e.g., about 0.2 to about 0.4 Watts, or more preferably, from about 0.08 Watts to about 0.3 Watts.

Suitable examples of commercially available thermistors include, but are not limited to, positive temperature coefficient (PTC) thermistors, e.g., self-regulating thermistors that draw less current as the temperature increases, available from, for example, Advanced Thermal Products, Inc. (St. Marys, Pa.).

Alternatively, as shown in, for example, FIG. 10, the heater 70 can comprise at least one conductive trace 58a, e.g., similar or identical to trace 58 as described with respect to the electrodes, e.g., reference electrode 52, above, wherein the heater has a suitable resistance. For example, in one embodiment, wherein the heater comprises a conductive trace and wherein the power source comprises a 6 volt battery, the resistance of the trace is in the range of from about 25 to about 75 ohms. In accordance with this illustrated embodiment, a portion of the conductive trace 58a is suitable for contacting the conductive contacts of the processing unit 99, e.g., at least one trace can include at least one contact pad 59a. Contact pad 59a can be similar or identical to contact pad 59, as described above. Each contact pad can be indistinguishable from the rest of the conductive trace, but more commonly (e.g., as shown in FIG. 10) has a larger width than other regions of the trace to facilitate a connection with the contacts on the processing unit. The contact pad can be made using the same material as the conductive traces and/or electrodes, but this is not necessary.

The heater can be sealed in and/or to the housing as is known in the art.

The above-identified components of the biological fluid analysis device, i.e., the power source, processing unit, and/or the indicator lamp(s), the biosensor, and the heater, can be mounted directly to the housing and/or a support member. For example, at least some components can be mounted to housing section 10d shown in FIG. 6b and housing section 10b as shown in FIG. 6e. However, other arrangements can also be suitable, for example, one or more of these components can be mounted to the support member 15 as shown in FIGS. 2, 6c, and 10.

Embodiments of the invention can include, for example, an on/off switch, but in more typical embodiments the operation of the biosensor begins upon engaging the contacts of the power source with the contacts of the processing unit by inserting the battery (or batteries) into the housing, or by removing an insulator between the respective contacts.

The biological fluid analysis device 100 (e.g., shown in FIGS. 2, 3, 6a, 6b, and 8a–8c); is especially suitable for use in closed biological fluid processing systems. Accordingly, the device is compatible with a variety of conventional sterilization protocols as are known in the art. One example of a suitable compatible sterilization protocol is gamma sterilization. In those embodiments wherein the enzyme is added to the device after the housing is assembled (e.g., wherein the enzyme is introduced through the sealable openings as described above) and after sterilization, the impermeable material prevents bacteria from entering the device. Moreover, laccase is a sterilizing agent, and the electrode cover 57 (FIG. 6b) provides an additional bacteria barrier preventing the passage of bacteria from the electrode chamber into the biological fluid in the analysis chamber. Alternatively, or additionally, handling the portions of the device carefully and efficiently during assembly (e.g., the housing sections can be essentially sterilely discharged from the mold for producing the housing) can reduce contamination, and the portions of the device can be exposed to, for example, a gas plasma discharge, just before assembly, to provide a sterile device. If desired (e.g., to check the assembly procedure for quality control purposes), samples of assembled devices can be tested by filling the analysis chambers with a sterile microorganism growth medium (e.g., broth) and operating the devices by connecting the power source. If after a desired period of time, for example, two days, there is no detectable change in the oxygen concentration in the chambers, the analysis devices are sterile.

In an embodiment, the biological fluid analysis device 100 is an element of a biological fluid processing system comprising one or more containers (e.g., flexible blood bags) for biological fluid. For example, a biological fluid (possibly containing microorganisms therein) can be processed to separate the biological fluid into one or more components, e.g., to provide transfusion products, and the analysis device can be placed in fluid communication with a source and/or storage container containing the biological fluid or separated component(s) therein. A portion of the potentially contaminated fluid can be passed into the biological fluid analysis device, and the oxygen consumed by the microorganisms (if a clinically significant level of microorganisms is present) can be detected as described above. If the device indicates the biological fluid in the analysis chamber does not contain a clinically significant level of bacteria, the biological fluid in the source and/or storage container can be further utilized, preferably, the fluid is transfused into a patient.

Typically, biological fluid is passed into the biological fluid analysis device using conventional blood processing techniques, for example, by creating a gravity head such that biological fluid passes from a container into the device, applying a force to the container (e.g., by compressing the container), or by stripping a conduit containing biological fluid therein to drive the fluid into the device. In other embodiments, e.g., involving an apheresis procedure, the apheresis system can be modified to provide for passing a portion of biological fluid into the device, preferably during the apheresis procedure.

In a preferred embodiment, the biological fluid analysis device is utilized to analyze a portion of filtered biological fluid, wherein the filtered biological fluid has been depleted of a level of at least one of platelets, white blood cells and red blood cells and the filtered biological fluid possibly contains microorganisms such as bacteria. As explained earlier, since components of the biological fluid (particularly platelets) consume oxygen, filtering the biological fluid reduces or eliminates the presence of these oxygen consuming components in the analysis chamber. As a result, "bacteria consumed oxygen" can be more accurately monitored.

Thus, an embodiment of a biological fluid processing system can include a biological fluid container, a filter assembly, and a biological fluid analysis device. In some embodiments, a biological fluid processing assembly comprising a filter assembly and a biological fluid analysis device can be provided, and the processing assembly can be incorporated into a biological fluid processing system, preferably while maintaining a closed system.

Accordingly, FIG. 9 shows an embodiment of a biological fluid processing assembly 400 comprising a biological fluid analysis device 100 (as described above) in fluid communication with a filter assembly 200 comprising a housing 210 having an inlet and an outlet and defining a fluid flow path between the inlet and the outlet, and a filter 250 comprising at least one porous filter element 255 comprising at least one porous medium across the fluid flow path. In this illustrated embodiment, the biological fluid processing assembly 400 also includes a conduit 307 interposed between the analysis device 100 and the filter assembly 200, and a conduit 306 communicating with the inlet of the filter assembly. In other embodiments, the processing assembly does not include either or both conduits. For example, in an embodiment, there is no conduit interposed between the device 100 and the assembly 200, e.g., the outlet of the filter assembly connects to the inlet 1 of the analysis device 100.

FIG. 9 also shows an embodiment of a biological fluid processing system 1000 comprising a first or source container 300 suitable for containing biological fluid (preferably a platelet-containing fluid such as platelet concentrate or apheresis platelets) therein, in fluid communication with the biological fluid processing assembly 400, wherein the system also includes a flow control device 350 such as a clamp, transfer leg closure, or valve interposed between the filter assembly 200 and the container 300. Alternatively, or additionally, the system can include a flow control device interposed between the filter assembly 200 and the biological fluid analysis device 100. Typically, the processing system 1000 includes additional containers (not shown) and biological fluid is passed from one of the containers through conduit 305 into container 300.

As noted above, biological fluid can be passed into the biological fluid analysis device using conventional processing techniques. For example, using the embodiment illustrated in FIG. 9 for reference, a force can be applied to the container 300 (e.g., by compressing the container), such that biological fluid passes from container 300 through the filter assembly 200 into the device 100. Alternatively or additionally, the container 300 can be inverted from the orientation shown in the Figure and held above the filter assembly and analysis device, creating a gravity head such that biological fluid passes from container 300 through the filter assembly 200 into the device 100.

If desired, the conduits 306 and/or 307 (containing biological fluid therein) can be stripped to drive the fluid into the device 100. In some embodiments, conduits 306 and/or 307 are arranged (e.g., by selecting the length and inner diameter) to be capable of containing a predetermined volume of biological fluid, so that stripping the conduit(s) drives a desired volume of fluid into the device. In other embodiments, e.g., involving an apheresis procedure, the apheresis system (not shown) can be modified to provide for passing a portion of biological fluid into the device.

Embodiments of the biological fluid processing system 1000 can include additional components such as at least one of an additional conduit, a leukocyte depletion filter, a connector, an additional container, and an additional vent (e.g., a gas inlet and/or a gas outlet).

In a preferred embodiment of a filter 250, the filter comprises at least one porous filter element 255 comprising a fibrous porous medium, and the filter element has a density of about 4000 g/ft³ or less (in some embodiments about 3800 g/ft³ or less), wherein the density is calculated according to the following equation, at a given average fiber diameter and voids volume:

$$\text{Density}(g/\text{ft}^3) = \frac{\begin{pmatrix} \text{basis weight of the fiber } (g/\text{ft}^2) \times \text{number} \\ \text{of layers in the filter element} \times (12 \text{ inches}/1 \text{ ft}) \end{pmatrix}}{(\text{thickness of the element (inches).})}$$

For example, suitable fibrous filter elements 255 according to some embodiments of the invention have a density in the range of from about 2550 g/ft³ to about 4000 g/ft³ (about 0.09 g/cm³ to about 0.14 g/cm³). In other illustrative embodiments, a fibrous filter element has a density in the range of from about 2550 g/ft³ to about 3200 g/ft³, or a density in the range of from about 3220 g/ft³ to about 4000 g/ft³.

Typically, the filter 250 removes at least some level of the white blood cells (and possibly other biological fluid components) by sieving. In some embodiments, the filter 250 also removes at least some level of white blood cells (and possibly other biological fluid components such as platelets) by adsorption.

Preferably, the filter reduces the level of platelets and white blood cells in the biological fluid passing therethrough by a factor of at least about 1 log for each component, and the reduction can be by a factor of at least about 2 logs. In some embodiments, the filter reduces the level of platelets by a level of at least one log, and reduces the level of white blood cells by a level of at least three logs.

The filter element 255 typically comprises a fibrous porous non-woven medium, more preferably a fibrous leukocyte depletion medium, even more preferably a fibrous synthetic polymeric leukocyte depletion medium comprising melt-blown fibers. Suitable filters and filter elements include, for example, those disclosed in International Application No. PCT/US0029543, filed Oct. 27, 2000.

A variety of materials can be used, including synthetic polymeric materials, to produce the porous media of the filter elements. Suitable synthetic polymeric materials include, for example, polybutylene terephthalate (PBT), polyethylene, polyethylene terephthalate (PET), polypropylene, polymethylpentene, polyvinylidene fluoride, polysulfone, polyethersulfone, nylon 6, nylon 66, nylon 6T, nylon 612, nylon 11, and nylon 6 copolymers.

Illustrative general techniques for preparing media from melt-blown fibers include, but are not limited to, those disclosed in, for example, U.S. Pat. Nos. 4,880,548; 4,925,572, 5,152,905, 5,443,743, 5,472,621, 5,582,907, and 5,670,060, as well as International Publication Nos. WO 91/04088 and WO 93/04763.

Typically, using the exemplary system 1000 illustrated in FIG. 9 for reference, the container 300, and the conduits 305–307, are made from commercially available materials used in biological fluid (e.g., blood) processing systems. More typically, they are made from plasticized materials, e.g., plasticized polyvinyl chloride (PVC). Exemplary plasticized PVC materials include, but are not limited to, PVC plasticized with dioctylphthalate (DOP), diethylhelxylphthalate (DEHP), or trioctyltrimelliate (TOTM), e.g., triethylhexyl trimellitate. The filter assembly housing 210 is also made from commercially available materials used in biological fluid (e.g., blood) processing systems, and can be made from the same material utilized for housing 10 of the biological fluid analysis device 100.

Using the embodiment illustrated in FIG. 9 for reference, the biological fluid analysis device 100 can remain attached to the other elements of the system (e.g., via conduit 307) during use. However, the device can be detached from the conduit, e.g., wherein a cord provides a tether between the device and the source container and/or the source container includes, for example, a strap, receptacle or retainer for the device. For example, conduits 307 and 306 can be heat-sealed and cut, and the filter assembly 200 can be discarded, and a cord attached to the device and source container allows the device to remain associated with the source container.

If desired, embodiments of the invention can include automated tracking and/or automated detection protocols and equipment. For example, one or more containers and the analysis device can include indicia (e.g., bar coding labels) with information such as the source(s) of the biological fluid, blood type, additive(s) utilized, an indication whether the change in oxygen level was reached, and this information can be tracked, combined with the detection results, and provided in whatever format is suitable, e.g., indicated (in machine readable form if desired) on at least one of the analysis chamber and the storage container and/or as a print-out.

EXAMPLE

Two biosensors are formed having the general configuration shown in FIG. 1 wherein the support member (15) is an adhesive-backed polyester film applied to a polycarbonate plate. Each biosensor (50) is prepared as follows.

The working electrode (51) and reference electrode (52) are screen printed onto an adhesive backed 0.003" thick polyester film. The working electrode (51) includes Ercon (Wareham, Mass.) Graphite Ink 0511D0502 (741801), and the reference electrode (52) includes Ercon Ag/AgCl Ink R-414 (DPM-68). The Ercon Ag/AgCl Ink R-414 is used to provide the traces (58) and contact pads (59).

The adhesive cover is removed from the polyester film, and the adhesive is placed in contact with a 0.063" nominal thickness clear polycarbonate plate. The film and plate form the support member (15).

A 0.25" hole is cut into a 0.5 mil thick double-faced tape (clear polyester film, acrylic adhesive) 57a. The adhesive cover is removed from one side of the tape, and the tape is adhered to the top of the polyester film having the screen printed electrodes thereon. The hole is located over the ends of the electrodes to provide the sensor area (electrode chamber 54).

Two holes (each 0.031" in diameter) are drilled into opposing portions of the sensor area (the 0.25" hole), without drilling through the electrode traces. The drill bit is passed through the screen printed film, and then the polycarbonate plate.

The adhesive cover is removed from the other side of the double-faced tape, and a 0.0005" high density polyethylene membrane (57) is placed over the sensor area. The membrane is arranged tautly over the sensor area, so that no wrinkles are present. The portion of the membrane over the sensor area forms the gas permeable portion (55) of the biosensor (50).

In order to clean and sterilize the electrodes, the sensor area is filled with a 3% hydrogen peroxide-water solution using a pipette to introduce the solution through one of the 0.031" holes. The air displaced by the solution is vented through the other 0.031" hole. The solution remains in the sensor area for about 25 minutes. Water is then introduced five times to wash the electrode surfaces.

The sensor area (54) is then filled with a laccase/electrolyte solution. The laccase is prepared from *Coriolus hirsutis* (available from the American Type Culture Collection (ATCC) under ATCC accession no. 66131) as generally described by Ghindilis et al. in *Biokhimiya* (Biochemistry) 53:65–639 (1988). The laccase/electrolyte solution is prepared by adding 10 μL of laccase (14 mg/ml) solution in 1:1 glycerol-sodium phosphate buffer (pH 6.5) to 60 μL of 0.1M sodium acetate buffer (pH 4.5) containing 0.03M KCl, before adding 30 μL of N,N'-dimethyl formamide.

The adhesive cover is removed from another adhesive backed 0.003" thick polyester film, and the film is placed over the holes in the polycarbonate plate to seal the biosensor.

Each biosensor is introduced into a side arm of a sterile 125 mL Cell-Stir flask containing a 110 ml suspension of leuko-reduced platelet concentrate inoculated with *Escherichia coli*. An oxygen electrode (Thermo Orion® (Beverly, Mass.) portable oxygen meter Model 810) is inserted into the center of the flask through a silicone cap. The platelet concentrate also includes 0.05% sodium polyanetholesulfonate. The flask contains a magnetic stirring bar.

The contact pads (59) of the electrodes (51 and 52) in the biosensor (50) are connected by wires to a high impedance amplifier that is attached to an analog-to-digital (A/D) converter and through an interface to a laptop computer. The oxygen electrode is also connected through an interface to another computer.

The side arms of the flask are sealed with silicone plugs.

The flask is placed on a magnetic stirrer, and the flask is maintained at a temperature of about 22.5° C. The system is turned on, and data are continuously acquired over the next 18 hours.

Samples are sterilely withdrawn at 0, 2, 4, 8 and 18 hours, diluted, and plated out in Trypticase Soy Agar. The agar plates are incubated for 24 hours at 37° C. in an incubator and the plates are then counted. By 20 hours the colony count has risen from $1 \times 10^3$ to $1 \times 10^8$ organisms.

At 0 hours, the potential of the working electrodes (with reference to the Ag/AgCl electrodes) is 400 mV (corresponding to an oxygen concentration of about 132 mm Hg as measured by the Orion® electrode) for both devices.

The potential of the working electrode in one device decreases to about 375 mV (oxygen concentration of about 128 mm Hg) at about 9.5 hours, with a further decrease to about 325 mV (oxygen concentration about 120 mm Hg) at about 15 hours, and a sharp decrease to about 150 mV (oxygen concentration about 90 mm Hg) by about 16 hours. After 18 hours, the potential of the working electrode is about 50 mV (corresponding to an oxygen concentration of about 72 mm Hg).

The potential of the working electrode in the other device decreases to about 360 mV (oxygen concentration about 125 mm Hg) at about 9.5 hours, with a further decrease to about 300 mV (oxygen concentration about 115 mm Hg) at about 15 hours, and a sharp decrease to about 175 mV (oxygen concentration about 95 mm Hg) by about 16 hours. After 18 hours, the potential of the working electrode the device is about 75 mV (oxygen concentration about 76 mm Hg).

The bacterial count rises from a count of $6 \times 10^3$ at 4 hours to a count of $1.3 \times 10^5$ at 8 hours.

This example shows the presence of *E. coli*, as indicated by the change in potential reflecting the change in oxygen concentration (at about 9 hours) can be detected utilizing a biosensor according to an embodiment of the invention.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A biological fluid analysis device comprising:
a housing including a biological fluid analysis chamber suitable for receiving a plasma-containing portion of biological fluid;
a vent communicating with the analysis chamber, the vent comprising a porous medium having a bacterial blocking pore rating; and
a biosensor communicating with the analysis chamber, the biosensor comprising an electrochemical-enzymatic sensor including a working electrode and a reference electrode, wherein the biosensor is arranged to monitor oxygen concentration in the analysis chamber over at least about a 4 hour time period; and
at least one visible marker that is activated while a change in oxygen concentration is monitored.

2. The device of claim 1, wherein the biosensor includes laccase.

3. The device of claim 1, including a self-contained power source.

4. The device of claim 3, wherein the first visible marker comprises a first indicator lamp that is activated when the oxygen concentration is monitored, the device further comprising at least a second indicator lamp that is either activated when, within a predetermined period of time, a decrease in oxygen concentration reaches a preset reference or threshold value, or the oxygen concentration does not reach a preset reference or threshold value.

5. The device claim 1, further comprising a heater arranged to raise the temperature of the plasma-containing fluid in the chamber over the ambient temperature for a desired period of time.

6. The device of claim 1, wherein the analysis chamber has an internal volume suitable for receiving about 10 ml of biological fluid or less.

7. The device of claim 6, wherein the internal volume is suitable for receiving about 2 to about 5 ml of biological fluid.

8. The device of claim 1, wherein the analysis chamber contains sodium polyanethol sulfonate.

9. A biological fluid analysis device comprising:
a housing including a biological fluid analysis chamber suitable for receiving a plasma-containing portion of biological fluid;
a vent communicating with the analysis chamber, the vent comprising a porous medium having a bacterial blocking pore rating; and
a biosensor communicating with the analysis chamber, the biosensor comprising an electrochemical-enzymatic sensor including a working electrode and a reference electrode, wherein the biosensor includes laccase and is arranged to detect oxygen concentration in the analysis chamber;
further comprising a flexible blood bag in fluid communication with the biological fluid analysis device.

10. The device of claim 9, arranged to monitor the oxygen concentration in the analysis chamber over a period of time.

11. The device of claim 10, arranged to monitor the oxygen concentration in the analysis chamber over at least about a 4 hour period of time.

12. The device of claim 11, further comprising at least one visible marker that is activated while the oxygen concentration is monitored.

13. The device of claim 9, arranged to detect a change in the oxygen concentration over at least about a 4 hour period of time.

14. The device of claim 13, further comprising at least one visible marker that is activated while a change in oxygen concentration is monitored.

15. The device of claim 9, further comprising at least a second visible marker that is activated when a decrease in oxygen concentration reaches a preset reference or threshold value.

16. The device of claim 9, comprising a first indicator lamp that is activated when the oxygen concentration is monitored, and at least a second indicator lamp that is activated when a decrease in oxygen concentration reaches a preset reference or threshold value.

17. The device of claim 16, wherein the first indicator lamp has a different visible wavelength than the second indicator lamp.

18. The device of claim 9, further comprising a heater arranged to raise the temperature of the plasma-containing fluid in the chamber over the ambient temperature for a desired period of time.

19. The device of claim 18, wherein the heater includes a thermistor.

20. The device of claim 18, wherein the heater includes a conductive trace.

21. A method for processing a biological fluid comprising:
passing a portion of a biological fluid into an analysis chamber of a biological fluid analysis device comprising: a housing including a biological fluid analysis chamber suitable for receiving a plasma-containing portion of biological fluid; a vent communicating with the analysis chamber, the vent comprising a porous medium having a bacterial blocking pore rating: and a biosensor communicating with the analysis chamber, the biosensor comprising an electrochemical-enzymatic sensor including a working electrode and a reference electrode, wherein the biosensor is arranged to monitor oxygen concentration in the analysis chamber;
detecting the oxygen concentration in the analysis chamber;
activating a first indicator lamp when a change in oxygen concentration is monitored; and
activating at least a second indicator lamp when a decrease in the oxygen concentration reaches a preset reference value.

22. The method of claim 21, including monitoring the oxygen concentration in the analysis chamber over at least about a 4 hour period of time.

23. The method of claim 21, including monitoring a change in the oxygen concentration in the analysis chamber over at least about a 6 hour period of time.

24. The method of claim 21, including raising the temperature of the biological fluid in the analysis chamber to at least about 30° C. for at least about 6 hours.

25. The method of claim 21, including passing the portion of biological fluid through a filter that allows microorganisms to pass through while depleting the fluid of at least one of leukocytes, red blood cells and platelets, before passing the portion of biological fluid into the analysis chamber.

26. A biological fluid analysis device comprising:
a housing including a biological fluid analysis chamber suitable for receiving a plasma-containing portion of biological fluid;

a vent communicating with the analysis chamber, the vent comprising a porous medium having a bacterial blocking pore rating; and a biosensor communicating with the analysis chamber, the biosensor comprising an electrochemical-enzymatic sensor including a working electrode and a reference electrode, wherein the biosensor is arranged to monitor oxygen concentration in the analysis chamber over at least about a 4 hour period of time; and at least one visible market that is activated while the oxygen concentration is monitored.

* * * * *